United States Patent
Hoft et al.

(10) Patent No.: US 12,247,053 B2
(45) Date of Patent: Mar. 11, 2025

(54) PEPTIDES FOR INDUCING HETEROSUBTYPIC INFLUENZA T CELL RESPONSES

(71) Applicants: Saint Louis University, St. Louis, MO (US); EpiVax, Inc., Providence, RI (US)

(72) Inventors: Daniel F. Hoft, St. Louis, MO (US); Christopher S. Eickhoff, St. Louis, MO (US); Annie De Groot, Providence, RI (US)

(73) Assignees: Saint Louis University, St. Louis, MO (US); EpiVax, Inc., Providence, RI (US)

( * ) Notice: Subject to any disclaimer, the term of this patent is extended or adjusted under 35 U.S.C. 154(b) by 993 days.

(21) Appl. No.: 17/288,133

(22) PCT Filed: Oct. 25, 2019

(86) PCT No.: PCT/US2019/057998
§ 371 (c)(1),
(2) Date: Apr. 23, 2021

(87) PCT Pub. No.: WO2020/086927
PCT Pub. Date: Apr. 30, 2020

(65) Prior Publication Data
US 2021/0380644 A1 Dec. 9, 2021

Related U.S. Application Data

(60) Provisional application No. 62/751,218, filed on Oct. 26, 2018.

(51) Int. Cl.
| | |
|---|---|
| A61K 39/39 | (2006.01) |
| A61K 9/19 | (2006.01) |
| A61K 39/145 | (2006.01) |
| C07K 14/11 | (2006.01) |
| A61K 39/00 | (2006.01) |

(52) U.S. Cl.
CPC ............. *C07K 14/11* (2013.01); *A61K 9/19* (2013.01); *A61K 39/145* (2013.01); *A61K 39/39* (2013.01); *A61K 2039/5154* (2013.01)

(58) Field of Classification Search
None
See application file for complete search history.

(56) References Cited

U.S. PATENT DOCUMENTS

| 5,591,430 A | 1/1997 | Townsend et al. |
| 9,265,822 B2 | 2/2016 | Hoft |
| 2002/0032162 A1 | 3/2002 | Content et al. |
| 2002/0147167 A1 | 10/2002 | Armstrong et al. |
| 2007/0025968 A1 | 2/2007 | Van Der Burg et al. |
| 2008/0032921 A1 | 2/2008 | Alexander et al. |
| 2010/0068224 A1 | 3/2010 | Crea et al. |
| 2011/0236967 A1 | 9/2011 | Wollan et al. |
| 2012/0121628 A1 | 5/2012 | Leng et al. |

FOREIGN PATENT DOCUMENTS

| WO | WO 1994/020127 | 9/1994 |
| WO | WO 1996/010631 | 4/1996 |
| WO | WO 1998/033888 | 8/1998 |
| WO | WO 1999/045954 | 9/1999 |
| WO | WO 2006/124408 | 11/2006 |
| WO | WO 2008/039267 | 4/2008 |
| WO | WO 2008/044032 | 4/2008 |

OTHER PUBLICATIONS

Appalla et al. (Accession No. GenBank AGU93020.1, 2013).*
Eickhoff et al. (Vaccine, Aug. 2019, p. 5371-5381).*
Assarsson et al. (Journal of Virology 2008, p. 12241-12251).*
Mils set al. (The Journal of Clinical Investigation, Apr. 2018, vol. 128, p. 1569-1580).*
Tan et al. (PLoS ONE, Jan. 2010, vol. 5, p. 1-11).*
Alexander et al., "Universal influenza DNA vaccine encoding conserved CD4+ T cell epitopes protects against lethal viral challenge in HLA-DR transgenic mice", Vaccine, 28:664-672, 2010.
De Groot et al., "Immunoinformatic comparison of T-cell epitopes contained in novel swine-origin influenza A (H1N1) virus with epitopes in 2008-2009 conventional influenza vaccine", Vaccine, 27(42):5740-7, 2009.
De Groot et al., "iVAX: A Sophisticated Suite of Online Vaccine Design Tools", I cubed Institute for Immunology & Informatics, Poster, EpiVax, Inc., 2013.
De Groot et al., "Immune camouflage: relevance to vaccines and human immunology", Human Vaccines & Immunotherapeutics, 10:3570, 2014.
Eickhoff et al., "Highly conserved influenza T cell epitopes induce broadly protective immunity", Vaccine, 37, pp. 5371-5381, 2019.
Heiny, et al., Evolutionarily Conserved Protein Sequences of Influenza A Viruses, Avian an dHuman as Vaccine Targets, PLoS One, 2(11):e1190, 2007.
Hoft, et al., "Live and Inactivated Influenza Vaccines Induce Similar Humoral Responses, but Only Live Vaccines Induce Diverse T-Cell Responses in Young Children", Journal Infectious Disease, 204, pp. 845-853, 2011.
Ichihashi et al., "Cross-protective peptide vaccine against influenza A viruses developed in HLA-A*2402 human immunity model", PLoS ONE, 6(9): e24626, 2011.

(Continued)

Primary Examiner — Agnieszka Boesen
(74) Attorney, Agent, or Firm — Parker Highlander PLLC

(57) ABSTRACT

The present invention provides compositions and methods for generation of an anti-influenza immune response. In particular, conserved T cell epitopes within matrix protein and nucleoprotein components of influenza virus have been identified and further screened for those structures that will bind either or both of HLA I and II molecules. Methods for vaccinating subjects with formulations of such peptides for the treatment or prevention of influenza infection also are described.

4 Claims, 5 Drawing Sheets

Specification includes a Sequence Listing.

(56) References Cited

OTHER PUBLICATIONS

Invitation to Pay Additional Fees for PCT/US2019/057998 dated Jan. 7, 2020, 2 pages.
International Search Report and Written Opinion for PCT/US2019/057998 dated Mar. 9, 2020, 13 pages.
Liu et al., "H7N9 T-cell epitopes that mimic human sequences are less immunogenic and may induce Treg-mediated tolerance", *Human Vaccines & Immunotherapeutics*, 11:2241, 2015.
McMurry et al., "A call to cellular & humoral arms: Enlisting cognate T cell help to develop broad-spectrum vaccines against influenza A", *human vaccines*, 4:2, 148-157, 2008.
Moise et al., "Universal H1N1 influenza vaccine development: identification of consensus class II hemagglutinin and neuraminidase epitopes derived from strains circulating between 1980 and 2011", *Human Vaccines & Immunotherapeutics*, 9(7):1598-607, 2013.
Moise et al., "Immunization with cross-conserved H1N1 influenza $CD4^+$ T-cell epitopes lowers viral burden in HLA DR3 transgenic mice", *Human Vaccines & Immunotherapeutics*, 9:2060, 2013.
Moise et al., "iVAX: An integrated toolkit for the selection and optimization of antigens and the design of epitope-driven vaccines", *Human Vaccines & Immunotherapeutics*, 11(9):2312-21, 2015.

* cited by examiner

FIGS. 1A-D

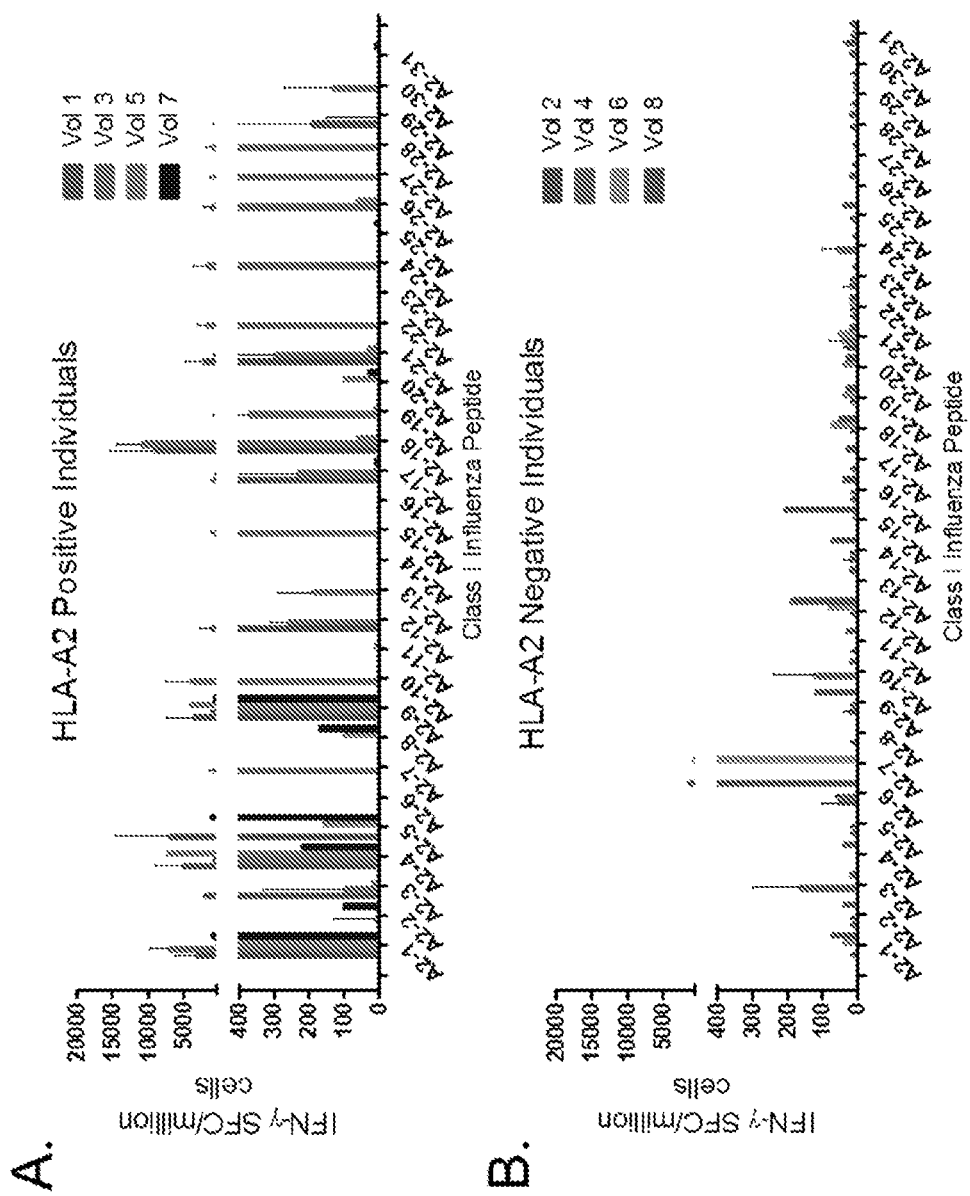
FIGS. 3A-B

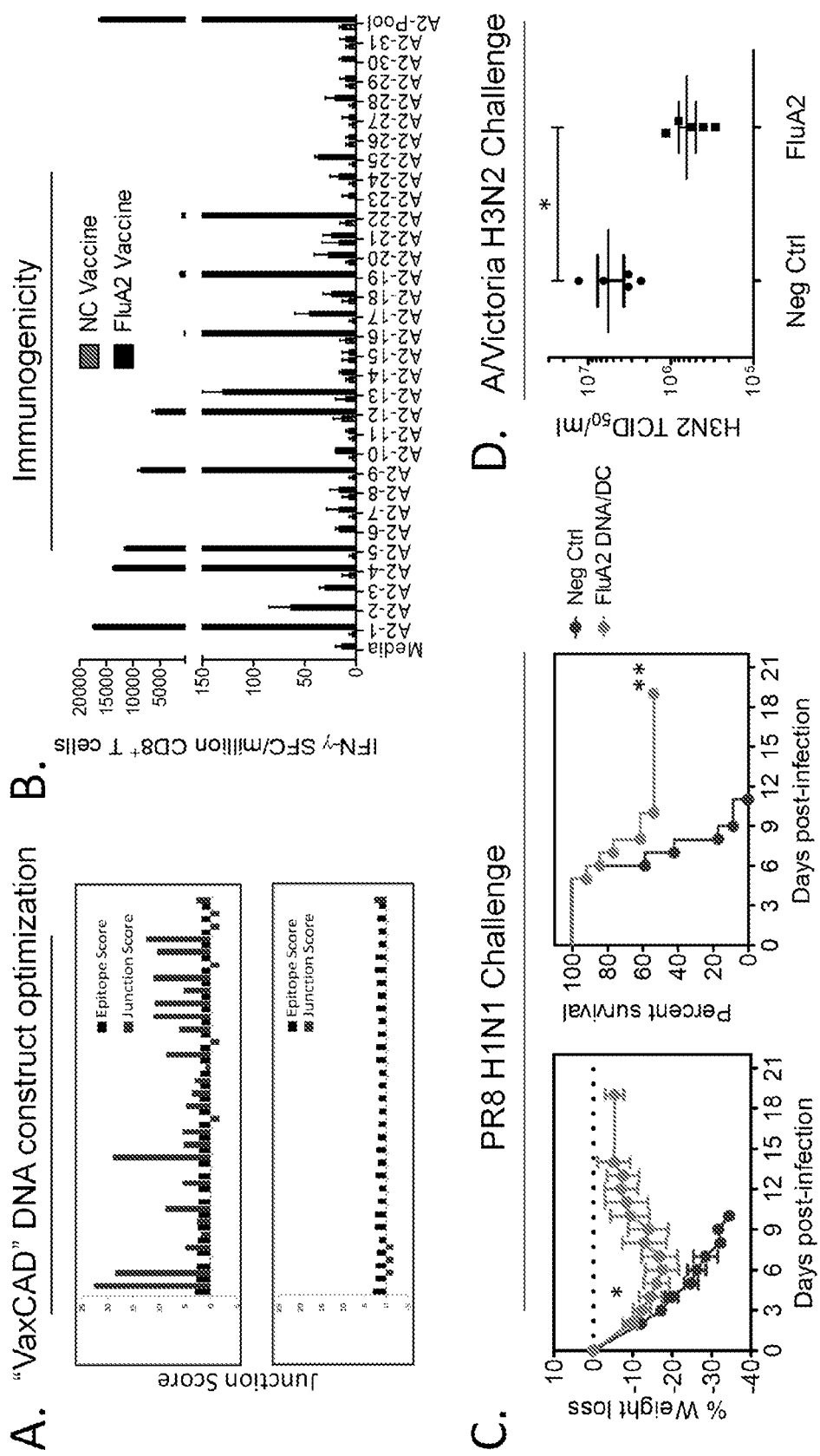
FIGS. 4A-D

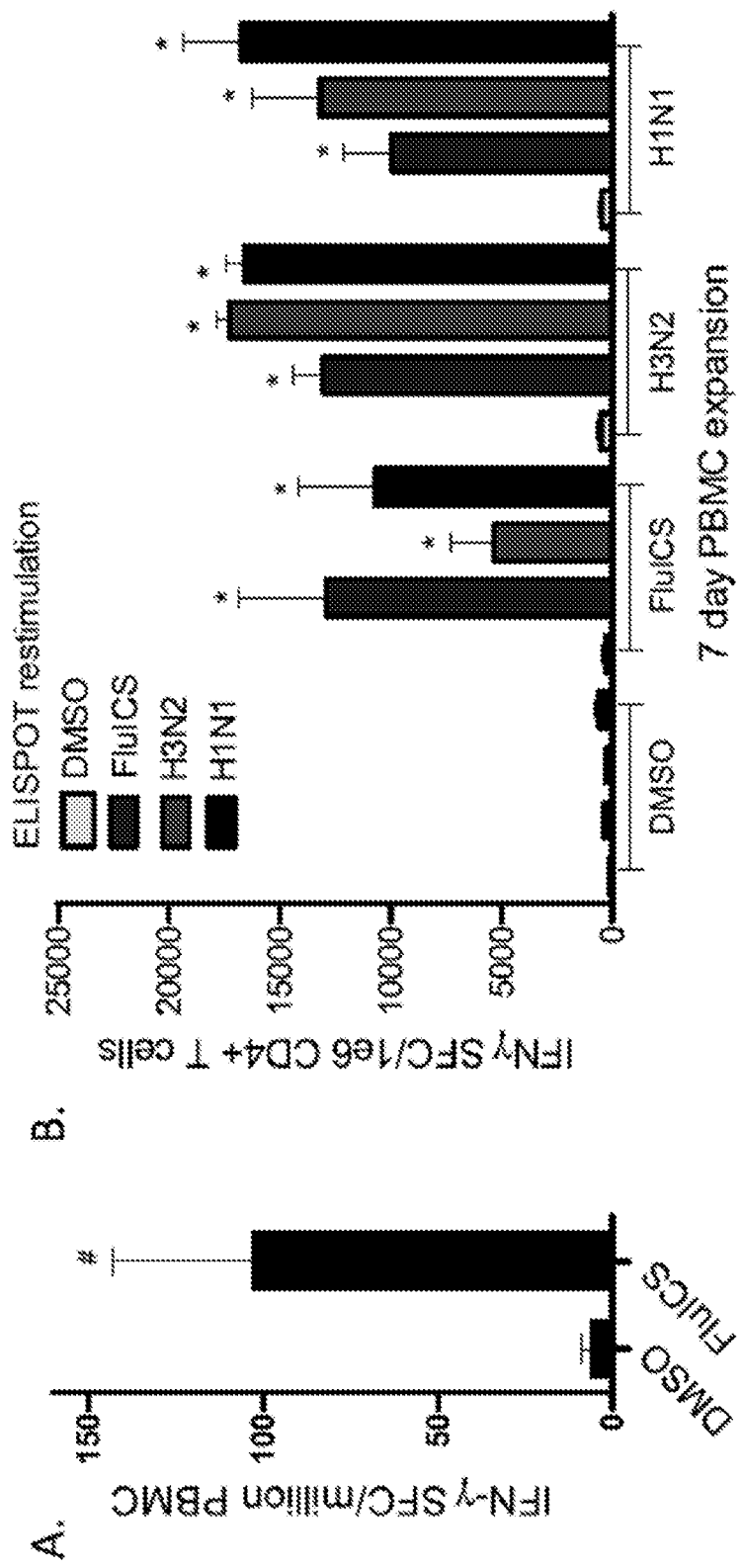
FIGS. 5A-B

SEQUENCE LISTING

```
<160> NUMBER OF SEQ ID NOS: 58

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide

<400> SEQUENCE: 1

Gly Met Leu Gly Phe Val Phe Thr Leu Thr Val Pro Ser Glu Arg Gly
1               5                   10                  15

Leu Gln

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Glu Asn Arg Met Val Leu Ala Ser Thr Thr Ala Lys Ala Met Glu Gln
1               5                   10                  15
```

Val

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Arg Arg Arg Phe Val Gln Asn Ala Leu Asn Gly Asn Gly Asp Pro Asn
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Gly Leu Ile Tyr Asn Arg Met Gly Ala Val Thr Thr Glu Ala Ala
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide

<400> SEQUENCE: 5

Leu Glu Asn Leu Gln Ala Tyr Gln Lys Arg Met Gly Val Gln Met Gln
1               5                   10                  15

Arg Phe

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Ser Gly Pro Leu Lys Ala Glu Ile Ala Gln Arg Leu Glu Asp Val
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Asn Pro Leu Ile Arg His Glu Asn Arg Met Val Leu Ala Ser Thr
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

```
Met Gly Ala Val Thr Thr Glu Val Ala Phe Gly Leu Val Cys Ala
1               5                   10                  15
```

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

```
Ala Ser Cys Met Gly Leu Ile Tyr Asn Arg Met Gly Ala Val Thr
1               5                   10                  15
```

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

```
Gln Pro Ala Phe Ser Val Gln Arg Asn Leu Pro Phe Glu Arg Val Thr
1               5                   10                  15

Ile
```

<210> SEQ ID NO 11
<211> LENGTH: 18
<212> TYPE: PRT
<213> ORGANISM: Artificial Sequence
<220> FEATURE:
<223> OTHER INFORMATION: Synthetic peptide

<400> SEQUENCE: 11

```
Lys Asp Glu Ile Arg Arg Ile Trp Arg Gln Ala Asn Asn Gly Glu Asp
1               5                   10                  15

Ala Thr
```

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

```
Asp Asn Glu Gly Arg Leu Ile Gln Asn Ser Leu Thr Ile Glu Arg Met
1               5                   10                  15

Val Leu
```

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

```
Leu Thr His Met Met Ile Trp His Ser Asn Leu Asn Asp Thr Thr Tyr
1               5                   10                  15

Gln Arg
```

<210> SEQ ID NO 14

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Arg Thr Ala Tyr Glu Arg Met Cys Asn Ile Leu Lys Gly Lys Phe
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic peptide

<400> SEQUENCE: 15

Arg Ser Ala Leu Ile Leu Arg Gly Ser Val Ala His Lys Ser Cys Leu
1               5                   10                  15

Pro

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Asp Ala Thr Tyr Gln Arg Thr Arg Ala Leu Val Arg Ser Gly Met
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide

<400> SEQUENCE: 17

Ile Gly Arg Phe Tyr Ile Gln Met Cys Thr Glu Leu Lys Leu Asn Asp
1               5                   10                  15

Tyr

<210> SEQ ID NO 18
<211> LENGTH: 18
<212> TYPE: PRT
<213> ORGANISM: Artificial Sequence
<220> FEATURE:
<223> OTHER INFORMATION: Synthetic peptide

<400> SEQUENCE: 18

Thr Met Val Met Glu Leu Ile Arg Met Ile Lys Arg Gly Ile Asn Asp
1               5                   10                  15

Arg Asn

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide

<400> SEQUENCE: 19
```

```
Leu Arg Ser Met Tyr Trp Ala Ile Arg Thr Arg Ser Gly Gly Asn Thr
1               5                   10                  15

Asn

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide

<400> SEQUENCE: 20

Ile Asp Pro Phe Arg Leu Leu Gln Asn Ser Gln Val Tyr Ser Leu Ile
1               5                   10                  15

Arg Pro

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide

<400> SEQUENCE: 21

Ser Gln Val Tyr Ser Leu Ile Arg Pro Asn Glu Asn Pro Ala His Lys
1               5                   10                  15

Ser Gln

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Arg Asn Phe Trp Arg Gly Glu Asn Gly Arg Lys Thr Arg Ser Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Arg Asn Lys Tyr Leu Glu Glu His Pro Ser Ala Gly Lys Asp Pro
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Pro Arg Met Cys Ser Leu Met Gln Gly Ser Thr Leu Pro Arg Arg
1               5                   10                  15

<210> SEQ ID NO 25
<211> LENGTH: 15
<212> TYPE: PRT
<213> ORGANISM: Artificial Sequence
```

<220> FEATURE:
<223> OTHER INFORMATION: Synthetic peptide

<400> SEQUENCE: 25

Glu Arg Met Cys Asn Ile Leu Lys Gly Lys Phe Gln Thr Ala Ala
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Gly Ile Leu Gly Phe Val Phe Thr Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Leu Leu Thr Glu Val Glu Thr Tyr Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Ala Leu Ala Ser Cys Met Gly Leu Ile
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Ile Leu Ser Pro Leu Thr Lys Gly Ile
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Ile Leu Gly Phe Val Phe Thr Leu Thr
1               5

<210> SEQ ID NO 31
<211> LENGTH: 9
<212> TYPE: PRT
<213> ORGANISM: Artificial Sequence
<220> FEATURE:

<223> OTHER INFORMATION: Synthetic peptide

<400> SEQUENCE: 31

Leu Ile Tyr Asn Arg Met Gly Ala Val
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Val Leu Ala Ser Thr Thr Ala Lys Ala
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Leu Thr Lys Gly Ile Leu Gly Phe Val
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Arg Met Val Leu Ala Ser Thr Thr Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Ala Leu Ser Tyr Ser Ala Gly Ala Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Leu Val Cys Ala Thr Cys Glu Gln Ile
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 37

Leu Gly Phe Val Phe Thr Leu Thr Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Val Thr Thr Glu Val Ala Phe Gly Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Lys Thr Arg Pro Ile Leu Ser Pro Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Gly Leu Ile Tyr Asn Arg Met Gly Ala
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Ile Leu His Leu Ile Leu Trp Ile Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Gly Ile Leu His Leu Ile Leu Trp Ile
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 43

Leu Ile Leu Trp Ile Leu Asp Arg Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Leu Leu Thr Glu Val Glu Thr Pro Ile
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Ile Leu Asp Arg Leu Phe Phe Lys Cys
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Trp Ile Leu Asp Arg Leu Phe Phe Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Ile Ile Gly Ile Leu His Leu Ile Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Arg Leu Phe Phe Lys Cys Ile Tyr Arg
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49
```

```
Arg Leu Ile Gln Asn Ser Leu Thr Ile
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Lys Leu Ser Asp Tyr Glu Gly Arg Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Gly Met Asp Pro Arg Met Cys Ser Leu
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Phe Leu Ala Arg Ser Ala Leu Ile Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Lys Leu Ser Thr Arg Gly Val Gln Ile
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Ile Leu Lys Gly Lys Phe Gln Thr Ala
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55
```

```
Leu Val Trp Met Ala Cys His Ser Ala
1               5
```

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

```
Ala Leu Ile Leu Arg Gly Ser Val Ala
1               5
```

<210> SEQ ID NO 57
<211> LENGTH: 445
<212> TYPE: PRT
<213> ORGANISM: Artificial Sequence
<220> FEATURE:
<223> OTHER INFORMATION: Synthetic polypeptide

<400> SEQUENCE: 57

```
Met Asp Ala Met Lys Arg Gly Leu Cys Cys Val Leu Leu Cys Gly
1               5                   10                  15

Ala Val Phe Val Ser Pro Ser Gly Thr Gly Ser Val Asp Glu Arg Met
                20                  25                  30

Cys Asn Ile Leu Lys Gly Lys Phe Gln Thr Ala Ala Gln Pro Ala Phe
            35                  40                  45

Ser Val Gln Arg Asn Leu Pro Phe Glu Arg Val Thr Ile Gly Met Leu
        50                  55                  60

Gly Phe Val Phe Thr Leu Thr Val Pro Ser Glu Arg Gly Leu Gln Arg
65                  70                  75                  80

Asn Phe Trp Arg Gly Glu Asn Gly Arg Lys Thr Arg Ser Ala Met Gly
                85                  90                  95

Ala Val Thr Thr Glu Val Ala Phe Gly Leu Val Cys Ala Ser Gly Pro
            100                 105                 110

Leu Lys Ala Glu Ile Ala Gln Arg Leu Glu Asp Val Leu Thr His Met
        115                 120                 125

Met Ile Trp His Ser Asn Leu Asn Asp Thr Thr Tyr Gln Arg Gly Leu
130                 135                 140

Ile Tyr Asn Arg Met Gly Ala Val Thr Thr Glu Ala Ala Ser Gln Val
145                 150                 155                 160

Tyr Ser Leu Ile Arg Pro Asn Glu Asn Pro Ala His Lys Ser Gln Pro
                165                 170                 175

Arg Met Cys Ser Leu Met Gln Gly Ser Thr Leu Pro Arg Arg Arg Arg
            180                 185                 190

Arg Phe Val Gln Asn Ala Leu Asn Gly Asn Gly Asp Pro Asn Arg Asn
        195                 200                 205

Lys Tyr Leu Glu Glu His Pro Ser Ala Gly Lys Asp Pro Arg Ser Ala
    210                 215                 220

Leu Ile Leu Arg Gly Ser Val Ala His Lys Ser Cys Leu Pro Leu Arg
225                 230                 235                 240

Ser Met Tyr Trp Ala Ile Arg Thr Arg Ser Gly Gly Asn Thr Asn Asn
                245                 250                 255

Pro Leu Ile Arg His Glu Asn Arg Met Val Leu Ala Ser Thr Ile Asp
            260                 265                 270

Pro Phe Arg Leu Leu Gln Asn Ser Gln Val Tyr Ser Leu Ile Arg Pro
        275                 280                 285
```

Lys Asp Glu Ile Arg Arg Ile Trp Arg Gln Ala Asn Gly Glu Asp
            290                 295                 300
Ala Thr Thr Met Val Met Glu Leu Ile Arg Met Ile Lys Arg Gly Ile
305                 310                 315                 320
Asn Asp Arg Asn Leu Glu Asn Leu Gln Ala Tyr Gln Lys Arg Met Gly
                325                 330                 335
Val Gln Met Gln Arg Phe Asp Asn Glu Gly Arg Leu Ile Gln Asn Ser
            340                 345                 350
Leu Thr Ile Glu Arg Met Val Leu Ile Gly Arg Phe Tyr Ile Gln Met
        355                 360                 365
Cys Thr Glu Leu Lys Leu Asn Asp Tyr Asp Ala Thr Tyr Gln Arg Thr
370                 375                 380
Arg Ala Leu Val Arg Ser Gly Met Glu Asn Arg Met Val Leu Ala Ser
385                 390                 395                 400
Thr Thr Ala Lys Ala Met Glu Gln Val Arg Thr Ala Tyr Glu Arg Met
                405                 410                 415
Cys Asn Ile Leu Lys Gly Lys Phe Ala Ser Cys Met Gly Leu Ile Tyr
            420                 425                 430
Asn Arg Met Gly Ala Val Thr His His His His His
            435                 440                 445

<210> SEQ ID NO 58
<211> LENGTH: 444
<212> TYPE: PRT
<213> ORGANISM: Artificial Sequence
<220> FEATURE:
<223> OTHER INFORMATION: Synthetic polypeptide

<400> SEQUENCE: 58

Met Gln Ile Phe Val Lys Thr Leu Thr Gly Lys Thr Ile Thr Leu Glu
1               5                   10                  15
Val Glu Pro Ser Asp Thr Ile Glu Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ser Asp Tyr Asn Ile Gln Lys Glu
    50                  55                  60
Ser Thr Leu His Leu Val Leu Arg Leu Arg Gly Ala Val Asp Gly Ile
65                  70                  75                  80
Leu Gly Phe Val Phe Thr Leu Ala Ala Tyr Gly Met Asp Pro Arg Met
                85                  90                  95
Cys Ser Leu Lys Leu Ser Asp Tyr Glu Gly Arg Leu Lys Leu Ser Thr
            100                 105                 110
Arg Gly Val Gln Ile Gly Leu Ile Tyr Asn Arg Met Gly Ala Ala Ala
        115                 120                 125
Tyr Gly Ile Leu His Leu Ile Leu Trp Ile Ala Tyr Arg Leu Ile
    130                 135                 140
Gln Asn Ser Leu Thr Ile Ala Ala Tyr Arg Met Val Leu Ala Ser Thr
145                 150                 155                 160
Thr Ala Ala Ala Tyr Lys Thr Arg Pro Ile Leu Ser Pro Leu Ala Ala
                165                 170                 175
Tyr Ala Leu Ala Ser Cys Met Gly Leu Ile Ala Ala Tyr Trp Ile Leu
            180                 185                 190
Asp Arg Leu Phe Phe Lys Ala Ala Tyr Phe Leu Ala Arg Ser Ala Leu
        195                 200                 205

-continued

```
Ile Leu Ala Ala Tyr Ile Leu Lys Gly Lys Phe Gln Thr Ala Ala Ala
    210                 215                 220

Tyr Ala Leu Ile Leu Arg Gly Ser Val Ala Ala Ala Tyr Val Thr Thr
225                 230                 235                 240

Glu Val Ala Phe Gly Leu Ala Ala Tyr Ala Leu Ser Tyr Ser Ala Gly
                245                 250                 255

Ala Leu Ala Ala Tyr Leu Val Trp Met Ala Cys His Ser Ala Ala Ala
            260                 265                 270

Tyr Leu Gly Phe Val Phe Thr Leu Thr Val Ala Ala Tyr Ile Leu Gly
        275                 280                 285

Phe Val Phe Thr Leu Thr Ala Ala Tyr Leu Ile Tyr Asn Arg Met Gly
    290                 295                 300

Ala Val Ala Ala Tyr Val Leu Ala Ser Thr Thr Ala Lys Ala Ala Ala
305                 310                 315                 320

Tyr Leu Val Cys Ala Thr Cys Glu Gln Ile Ala Ala Tyr Ile Leu Ser
                325                 330                 335

Pro Leu Thr Lys Gly Ile Ala Ala Tyr Leu Thr Lys Gly Ile Leu Gly
            340                 345                 350

Phe Val Ala Ala Tyr Leu Leu Thr Glu Val Glu Thr Pro Ile Ala Ala
        355                 360                 365

Tyr Leu Leu Thr Glu Val Glu Thr Tyr Val Ala Ala Tyr Leu Ile Leu
    370                 375                 380

Trp Ile Leu Asp Arg Leu Ala Ala Tyr Arg Leu Phe Phe Lys Cys Ile
385                 390                 395                 400

Tyr Arg Ala Ala Tyr Ile Ile Gly Ile Leu His Leu Ile Leu Ala Ala
                405                 410                 415

Tyr Ile Leu Asp Arg Leu Phe Phe Lys Cys Ala Ala Tyr Ile Leu His
            420                 425                 430

Leu Ile Leu Trp Ile Leu His His His His His His
        435                 440
```

PEPTIDES FOR INDUCING HETEROSUBTYPIC INFLUENZA T CELL RESPONSES

REFERENCE TO RELATED APPLICATIONS

The present application is a national phase application under 35 U.S.C. § 371 of International Application No. PCT/US2019/057998, filed Oct. 25, 2019, which claims the priority benefit of U.S. provisional application No. 62/751,218, filed Oct. 26, 2018, the entire contents of each of which are incorporated herein by reference.

STATEMENT REGARDING FEDERALLY SPONSORED RESEARCH

This invention was made with government support under Grant No. R21 AI105605 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Oct. 1, 2019, is named USTLP0079WO_ST25.txt and is 20.4 kilobytes in size.

BACKGROUND

1. Field

The present invention relates generally to the fields of virology and immunology. More particularly, it concerns the identification of T-cell epitopes and the development of dendritic cell and DNA vaccines for the treatment and prevention of influenza.

2. Description of Related Art

It is estimated that 250,000-500,000 deaths occur annually due to influenza (WHO, 2014). Each flu season, 5% to 10% of adults and 20% to 30% of children are infected with circulating flu strains. Influenza viruses undergo high mutation rates within the hemagglutinin (HA) and neuraminidase (NA) sequences, causing antigenic drift and partial escape from pre-existing flu immunity. The more dramatic and abrupt changes in viral composition lead to pandemics and more severe disease because human populations have limited cross-protective immunity to the new reassortments (Bleshe, 2005). The 1918 Spanish flu pandemic, resulting from a newly emerged avian-like influenza strain, infected 20%-40% of the world's population and resulted in at least 50-100 million deaths (Taubenberger & Morens, 2006). Other pandemics occurred in 1957 (H2N2), 1968 (H3N2), and 2009 (H1N1), with the most recent 2009 strain infecting >60 million people in the U.S. alone (Shrestha et al., 2011). Currently, avian H5 and H7 strains represent major public health threats that could lead to unprecedented morbidity and mortality. In 2013-2014, new H7 avian influenza virus strains infected humans in China (Burke & Trock, 2018). These strains were highly virulent, killing roughly ⅓-½ of those infected. Fortunately, these H7 strains have not yet evolved for efficient human to human transmission (Fang et al., 2013). However, international public health officials agree there is significant risk to public health should H7 viruses evolve to become efficiently transmitted from person-to-person.

Licensed influenza vaccines currently focus on inducing neutralizing antibodies against seasonal viruses. A major limitation of this approach is the focus on strain-specific immunity that rarely induces optimal immunity against drifted strains that emerge from one flu season to the next. Even during a single flu season, viral drift can occur, which may make a newly generated seasonal influenza vaccine ineffective against the new strains (occurring most recently in 2014-2015 when most H3N2 isolates were antigenically different from the vaccine strain). A major consequence of targeting seasonal influenza strains is variable influenza vaccine effectiveness (VE), ranging from as low as 10% to 60% over the last decade (Treanor et al., 2012; Belongia et al., 2009; CDC, 2016). The predominant influenza vaccines used over the past >30 years are composed of inactivated purified components of split virions formulated to induce strain-specific anti-HA antibodies. Recombinant HA vaccines (rHA) and live attenuated influenza vaccines (LAIV; administered intranasally) have also been used extensively over the past several years. LAIV induces responses against internal viral proteins (unlikely to be effective targets of protective antibody responses), including T cells directed against conserved internal epitopes that can provide more broadly protective heterotypic immunity. LAIV has been shown to induce better protection in children (Belshe et al., 2007), potentially as a result of more broadly heterotypic T cell immunity (Belshe & Gruber, 2000).

T cells provide heterotypic protective immunity in both mice and humans (Schulman & Kilbourne, 1965; Liang et al., 1994; Benton et al., 2001; McMichael et al., 1983; Sonoguchi et al., 1985; Epstein, 2006). Infection induces heterotypic immunity that relies on both $CD4^+$ and $CD8^+$ T cells (Schulman & Kilbourne, 1965; Liang et al., 1994). Furthermore, B cell knockout mice, unable to produce antibodies, develop protective heterotypic immunity after immunization by low dose respiratory infection (Benton et al., 2001). In addition, DNA vaccines expressing the internal influenza proteins nucleoprotein (NP) and matrix 1 and 2 (M1/2) have induced heterotypic T cell immunity (Mbawuike et al., 1994), including protective immunity directed against avian H5 strains (Ulmer et al., 1998; Epstein et al., 2002). Overall these studies demonstrate that T cell-mediated heterotypic immunity can be protective against severe morbidity and death in mice.

Influenza-specific T cell-mediated heterotypic protective immunity also develops in humans. In 1983, McMichael demonstrated that human $CD8^+$ CTL can recognize diverse influenza strains (McMichael et al., 1983). It was more recently demonstrated that U.S. adults had both $CD4^+$ and $CD8^+$ T cells reactive with avian H5N1 viral sequences despite the absence of previous H5N1 exposure (Jameson et al., 1999). Also, children 6-35 months old develop T cells specific for highly conserved epitopes after LAIV vaccination (Hoft et al., 2011). Perhaps the best data supporting T cell-mediated heterotypic immunity in humans has been derived from epidemiological studies, documenting that persons previously infected with unrelated influenza strains are partially protected against pandemic strains without cross-neutralizing antibodies (Sonoguchi et al., 1985; Epstein, 2006).

The integration of the fields of bioinformatics and vaccinology has made possible the development of protective T cell-targeted multi-epitope vaccines. Immunoinformatic identification of conserved T cell epitopes in variola and vaccinia genomes (Moise et al., 2009) has been utilized to generate an epitope-based vaccine with demonstrated efficacy against poxviral lethal challenges in mice (Moise et al., 2011). Furthermore, additional research has demonstrated that vaccines inducing responses against even a single T cell epitope can be sufficient to induce potent protection against virulent pathogen challenge (Moutaftsi et al., 2006). T cell-targeted influenza and tularemia vaccines also have been shown to induce protective immunity against relevant pulmonary influenza and *Francisella tularensis* challenges, respectively (McMurry et al., 2007; Gregory et al., 2009; Moise et al., 2013). However, there remains a need for influenza vaccines that induce influenza-specific T cell-mediated heterotypic immunity in humans.

SUMMARY

Provided herein are immunoinformatic tools to identify promiscuous CD4+ T cell epitopes and HLA-A2-restricted CD8+ T cell epitopes highly conserved in widely diverse influenza A strains. The identified universally relevant T cell epitopes induce potent protection in HLA transgenic mice against both H3N2 and H1N1 viral challenges.

In one embodiment, provided herein are peptides comprising at least two amino acid sequences selected from the group consisting of SEQ ID NOs: 26-56. In some aspects, the at least two amino acid sequences are each 9-15 residues in length. In some aspects, the at least two amino acids are juxtaposed. In some aspects, the peptide is fused to another amino acid sequence. In some aspects, the peptide is lyophilized. In some aspects, the peptide is formulated in a pharmaceutically acceptable buffer, diluent, or excipient. In certain aspects, the peptide comprises five or more, ten or more, fifteen or more, twenty or more, twenty-five or more, thirty or more, or thirty-one amino acid sequences selected from the group consisting of SEQ ID NOs: 26-56. In certain aspects, the peptide comprises all of the amino acid sequences in the group consisting of SEQ ID NOs: 26-56. In certain aspects, the peptide has a sequence according to SEQ ID NO: 58. In one embodiment, nucleic acids encoding the peptides of the present embodiment are provided. In some aspects, the nucleic acids further comprise a promoter operably linked to the nucleic acid encoding the peptide.

In one embodiment, peptides are provided comprising at least two amino acid sequences selected from the group consisting of SEQ ID NOs: 1-25. In some aspects, the at least two amino acid sequences are each 12-20 residues in length. In some aspects, the at least two amino acids are juxtaposed. In some aspects, the peptide is fused to another amino acid sequence. In some aspects, the peptide is lyophilized. In some aspects, the peptide is formulated in a pharmaceutically acceptable buffer, diluent or excipient. In certain aspects, the peptide comprises five or more, ten or more, fifteen or more, twenty or more, or twenty-five amino acid sequences selected from the group consisting of SEQ ID NOs: 1-25. In some aspects, the peptide comprises all of the amino acid sequences in the group consisting of SEQ ID NOs: 1-25. In certain aspects, the peptide has a sequence according to SEQ ID NO: 57. In one embodiment, nucleic acids encoding the peptides of the present embodiment are provided. In some aspects, the nucleic acids further comprise a promoter operably linked to the nucleic acid encoding the peptide.

In one embodiment, compositions are provided comprising at least two unique peptides each having an amino acid sequence selected from the group consisting of SEQ ID NOs: 26-56. In some aspects, the at least two peptides are each 9-15 residues in length. In some aspects, the composition is lyophilized. In some aspects, the composition comprises five or more, ten or more, fifteen or more, twenty or more, twenty-five or more, thirty or more, or thirty-one unique peptides each having an amino acid sequence selected from the group consisting of SEQ ID NOs: 26-56. In some aspects, the composition is formulated in a pharmaceutically acceptable buffer, diluent, or excipient.

In one embodiment, compositions comprising antigen presenting cells presenting at least two unique peptides each having an amino acid sequence selected from the group consisting of SEQ ID NOs: 26-56. In some aspects, the antigen presenting cells are presenting five or more, ten or more, fifteen or more, twenty or more, twenty-five or more, thirty or more, or thirty-one unique peptides each having an amino acid sequence selected from the group consisting of SEQ ID NOs: 26-56. In some aspects, the composition is formulated in a pharmaceutically acceptable buffer, diluent, or excipient.

In one embodiment, compositions are provided comprising at least two unique peptides each having an amino acid sequence selected from the group consisting of SEQ ID NOs: 1-25. In some aspects, the at least two peptides are each 12-20 residues in length. In some aspects, the composition is lyophilized. In some aspects, the composition comprises five or more, ten or more, fifteen or more, twenty or more, or twenty-five unique peptides each having an amino acid sequence selected from the group consisting of SEQ ID NOs: 1-25. In some aspects, the composition is formulated in a pharmaceutically acceptable buffer, diluent, or excipient.

In one embodiment, compositions are provided comprising antigen presenting cells presenting at least two unique peptides each having an amino acid sequence selected from the group consisting of SEQ ID NOs: 1-25. In some aspects, the antigen presenting cells are presenting five or more, ten or more, fifteen or more, twenty or more, or twenty-five unique peptides each having an amino acid sequence selected from the group consisting of SEQ ID NOs: 1-25. In some aspects, the composition is formulated in a pharmaceutically acceptable buffer, diluent, or excipient.

In one embodiment, methods are provided of inducing an immune response in a subject comprising administering to a subject a peptide of any one of the present embodiments; a nucleic acid of any one of the present embodiments; or a composition of any one of the present embodiments. In some aspects, the methods may comprise administering more than one peptide of the present embodiment, more than one nucleic acid of the present embodiments, or more than one composition of the present embodiments. In some aspects, the methods may comprise administering a combination of one or more peptide of the present embodiments, one or more nucleic acid of the present embodiments, and/or one or more composition of the present embodiments. In these aspects, each peptide, nucleic acid, and/or composition administered may be administered simultaneously or sequentially.

In some aspects, administration comprises injection. In certain aspects, injection comprises subcutaneous or intramuscular injection. In some aspects, administration comprises inhalation. In certain aspects, inhalation comprises inhaling a nasal aerosol or mist.

In some aspects, the methods further comprise administering an adjuvant to the patient. In certain aspects, the adjuvant is a squalene adjuvant, a cytokine adjuvant, a lipid adjuvant, or a TLR ligand. In some aspects, the peptide, nucleic acid, or composition is administered at least a second time. In some aspects, the methods further comprise administering a live-attenuated vaccine or a killed vaccine to the subject. In some aspects, the subject is a human subject. In some aspects, the methods further comprise measuring a $CD4^+$, a $CD8^+$, and/or a γδ T cell response in the subject following administration.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A—female HLA-DR1 transgenic mice were vaccinated i.m. twice 2 weeks apart with a DNA vaccine encoding the 25 highly conserved influenza A ICS (FluICS) detailed in Table 1. These mice were additionally vaccinated with mature HLA-DR1 transgenic dendritic cells pulsed with these same epitopes. Shown are splenic $CD4^+$ T cell IFN-γ ELISPOT responses determined 4 weeks after final vaccination, and 4 days post-intranasal A/PR/8 H1N1 (pooled cells from groups of n=2 mice). The left column of each pair represents "NC DNA/DC"; the right column of each pair represents "FluICS DNA/DC. " FIGS. 1B-D—HLA-DR1 transgenic mice were immunized 4 times with control or FluICS DNA vaccines. Four weeks post-vaccination mice were challenged intranasally with $30 \times LD_{50}$ Influenza A/Victoria/3/75 (H3N2). FIG. 1B shows total splenocyte IFN-γ ELISPOT results obtained 4 days post-challenge (n=3 female mice/group). Protection against H3N2 challenge was assessed 3 days post-infection by lung homogenate $TCID_{50}$ assay (FIG. 1C; n=3 female mice/group) and by survival (FIG. 1D; n=8 mixed sex mice/group). *P<0.005 by unpaired t-test, P=0.012 by paired t test, and *P=0.039 by 1-tailed Fisher's exact test.

FIGS. 3A-B. Human immunogenicity of highly conserved HLA-A2 restricted influenza A epitopes. PBMCs from HLA-A2 positive and HLA-A2 negative individuals were cultured with DMSO alone or with individual putative influenza A HLA-A2-restricted epitopes for 2 weeks with IL-2 provided on days 0, 2, 7, and 10. On day 14 of culture, cells were washed and added to IFN-γ ELISPOT assays (50,000 cells/well) with the same peptide as utilized for expansion. Shown are results [expressed as spot forming cells (SFC) per million cells] obtained from PMBCs collected from four HLA-A2 positive (FIG. 3A-top) and four HLA-A2 negative (FIG. 3B-bottom) individuals (DMSO expansion subtracted). In FIG. 3A, the four columns in each set represent, from left to right, Vol 1, Vol 3, Vol 5, and Vol 7. In FIG. 3B, the four columns in each set represent, from left to right, Vol 2, Vol 4, Vol 6, and Vol 8.

FIGS. 4A-D. Heterotypic protective immunity induced by vaccines incorporating highly conserved influenza epitopes. DNA vaccines encoding 31 highly conserved influenza A HLA-A2 epitopes were designed using a computer assisted vaccine design tool (VaxCAD). Shown in FIG. 4A are predicted immunogenicity scores of selected epitopes (the left bar of each pair) and junctions (the right bar of each pair) of minigenes arranged by default order (top) and by VaxCAD (bottom). HLA-A2 transgenic mice were vaccinated i.m. with DNA encoding the HLA-A2-restricted conserved T cell epitopes (or control insert), and boosted with peptide-pulsed DC vaccines (delivered i.v.). $CD4^+$ T cell help was provided to all mice by co-immunization with DNA and DC vaccines incorporating OVA and PADRE epitopes. One month following the final vaccination groups of mice were euthanized to study vaccine-induced T cell immunity. Shown in FIG. 4B are results from IFN-γ ELISPOT assays using purified $CD8^+$ T cells stimulated with APCs pulsed with individual (and pooled) peptides (n=3 male HLA-A2$^+$ mice/group). The left column of each pair represents "NC Vaccine"; the right column of each pair represents "FluA2 Vaccine." In FIG. 4C, groups of control and FluA2 vaccinated mice were challenged with $8 \times LD_{50}$ of Influenza A/PR/8 H1N1, and post-challenge weights (left) and survival (right) monitored. Shown are results of two combined experiments with similar outcomes (combined sexes, n=12-

13 mice per group). In FIG. 4D, groups of vaccinated mice were challenged with nonlethal A/Victoria H3N2 ($1\times10^5$ $TCID_{50}$). Four days later, viral burdens were assessed in lung homogenates by $TCID_{50}$ assay (n=5 female mice/group). *P<0.05 by Mann-Whitney U test, ** P<0.005 by Fisher's exact and Mantel-Cox log rank tests.

FIGS. 5A-B. Human CD4+ T cell immunogenicity of highly conserved class II immunogenic consensus sequences. (FIG. 5A) PBMC from four volunteers were stimulated in overnight IFN-γ ELISPOT assays with either DMSO alone (control) or FluICS peptides. (FIG. 5B) PBMC from five volunteers were expanded in vitro with DMSO (control), FluICS peptides, or live IAV for 1 week. Then CD4+ T cells were isolated and stimulated in IFN-γ ELISPOT assays with APCs pulsed with DMSO, FluICS peptides, or live IAV (H1N1 and H3N2). Data depicted as means±standard errors. #P<0.05 by Mann-Whitney U test, *P≤0.05 by Mann-Whitney U and matched pair t-tests.

DETAILED DESCRIPTION

Figure 1:
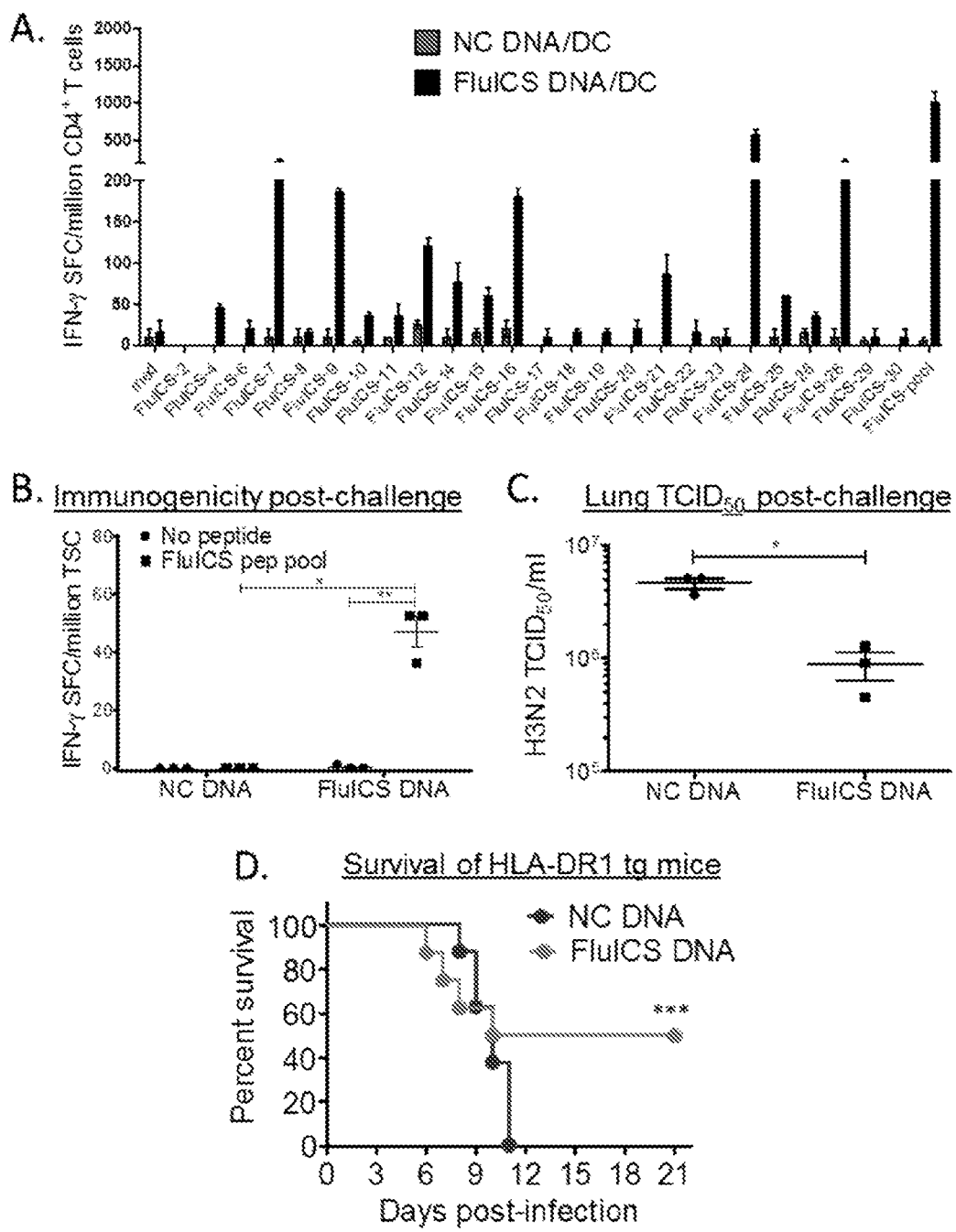
FIGS. 1A-D. Immunogenicity and protective efficacy of highly conserved class II immunogenic consensus sequences (ICS) in HLA-DR1 transgenic mice.

Influenza world-wide causes significant morbidity and mortality annually, and more severe pandemics when novel strains evolve to which humans are immunologically naïve. Because of the high viral mutation rate, new vaccines must be generated based on the prevalence of circulating strains every year. New influenza vaccination approaches are urgently needed to induce more broadly protective immunity for guarding the population against potential influenza pandemics. A comprehensive strategy to develop T cell-targeting influenza vaccines with universal significance was developed. Immunoinformatic tools were used to identify pan-HLA-DR and HLA-A2 supertype-restricted T cell epitopes highly conserved among >50 widely diverse influenza A strains (representing hemagglutinin types 1, 2, 3, 5, 7, and 9). Conserved influenza peptides predicted to be class I epitopes restricted by HLA-A2 were found to be immunogenic in HLA-A2 positive but not HLA-A2 negative individuals. Dendritic cell and DNA vaccines expressing these epitopes were generated and tested in HLA transgenic mice. These vaccines were highly immunogenic, and were significantly protective against both H1N1 and H3N2 influenza challenges. Conserved T cell epitopes expressed by widely diverse influenza strains can induce broadly protective, heterotypic influenza immunity, providing strong support for further development of universally relevant T cell-targeting influenza vaccines.

I. ASPECTS OF THE PRESENT EMBODIMENTS

The development of universal influenza vaccines protective against both future seasonal and pandemic viruses is considered a top priority by public health programs worldwide (Erbelding et al., 2018). Tens of thousands of people die from seasonal influenza in the U.S. alone every year, and influenza pandemics have killed up to 50-100 million people during the first 1-2 years of circulation of novel viral strains in human populations, and threaten to do so again. Current seasonal vaccines can be effective but need to be given every year because the circulating viruses mutate rapidly. Vaccine manufacturers in collaboration with public health epidemiologists must predict what will become the most important circulating strains in advance of each influenza season, leaving only a few months to make enough vaccine in time. Sometimes the predictions are wrong leading to major mismatches between antigenic targets expressed by circulating influenza strains causing disease and the vaccines designed to induce protection. These problems exist because all conventional influenza vaccines target the most rapidly mutating but strongly immunogenic surface antigens, hemagglutinin and neuraminidase. Novel vaccines that induce immunity against highly conserved influenza sequences are urgently needed.

The results presented here provide for a potentially paradigm-shifting T cell targeting vaccination strategy that could induce protection against all past and future influenza A viruses in virtually all people worldwide. First, highly conserved sequences were identified in influenza strains representing all past pandemic strains, dozens of seasonal strains, and even avian strains (e.g., H5 and H7 strains) that are currently considered the highest risks for future pandemics with the potential for loss of life surpassing the 1918 H1N1 pandemic. Next, cutting-edge immunoinformatic tools were used to identify predicted T cell epitopes within the highly conserved sequence subset based on motifs known to be important for binding to HLA molecules required for presentation to T cells. Epitope predictions were confirmed both in HLA transgenic mice and with human peripheral blood lymphocytes. New DNA vaccines were made encoding strings of highly conserved and immunogenic T cell epitopes. These novel vaccines induced protection in HLA transgenic mice against diverse influenza strains. These results clearly demonstrate that vaccines incorporating highly conserved influenza A epitopes can provide broad protection against diverse influenza viruses, confirming the relevance of this strategy for generating novel universal influenza vaccines.

Vaccines encoding putative promiscuous HLA-DR ICS were immunogenic and efficacious against H3N2 influenza challenge in HLA-DR1 transgenic mice, as measured both by survival and lung viral burdens. Importantly, these HLA-DR ICS vaccines were designed to contain epitopes capable of stimulating only CD4+ helper T cells and thus demonstrate that vaccines targeting only CD4+ T cell responses, and not neutralizing antibodies or CD8+ cytotoxic T cells, could provide protection. Memory CD4+ T cells induced by this vaccine could facilitate more rapid induction of neutralizing antibody and/or CD8+ T cell responses that develop during influenza viral challenge. Alternatively, cytokines produced by memory/effector CD4+ T cells could increase intracellular resistance to viral replication, and/or these CD4+ T cells could mediate Fas/Fas-ligand pro-apoptotic signaling in influenza infected cells. Although these experiments have focused on protection in HLA-DR1 transgenic mice, it is anticipated that these vaccines will provide broad immunogenicity in diverse HLA-DR transgenic mice and >95% of all humans. Previous studies utilizing the same immunoinformatic toolkit to identify panDR-restricted ICS indicate that this is an achievable goal and is likely to be the case with this predicted ICS (Moise et al., 2013; De Groot et al., 2011; Koita et al., 2006). Additional work using transgenic mice that express a broader panel of distinct HLA-DR alleles, and PBMC from diverse human populations expressing distinct HLA-DR alleles are ongoing to confirm the promiscuous immunogenicity of the conserved influenza ICS identified here.

Vaccines encoding highly conserved, influenza-specific and HLA-A2 supertype-restricted CD8+ T cell epitopes were constructed in parallel with the promiscuous HLA-DR ICS encoding vaccines. The HLA-A2 supertype is the most common of the six HLA class I supertypes that cover more than 95% of the world's population. In fact, HLA-A2 is expressed by 40%-60% of all humans worldwide. Therefore, these studies were performed first with the HLA-A2 supertype. Similar to the strategy described above for identification of HLA-DR epitopes, the highly conserved influenza genome sequence subset was identified, HLA-A2 supertype peptide binding was predicted, and the immunogenicity as well as protective capacity of predicted epitopes in HLA-A2 transgenic mice was studied. Immunogenicity in humans expressing HLA-A2 was also confirmed. We anticipated that most of the predicted HLA-A2 epitopes would bind to HLA-A2, and of those which bound HLA-A2, many would prove to be immunogenic in HLA-A2 transgenic animals and/or human samples. Overall, approximately 50% of our HLA-A2 supertype epitope predictions were confirmed in both HLA transgenic mice and human PBMC assays. It is important to point out that even though a given peptide may bind to a specific MHC, there may not be T cells in the periphery that could recognize the specific MHC:peptide complex (De Groot et al., 2002). In addition, it is expected that immunogenicity results obtained from HLA-A2 transgenic mice will not completely match those obtained from HLA-A2 supertype positive individuals since mice did not evolve with HLA and there are differences in T cell selection and the T cell receptor (TCR) repertoire between mice and humans. Therefore, the results detected in HLA transgenic mouse models are an underestimate of the epitopes that could be immunogenic in humans. Indeed, most of the predicted HLA-A2 epitopes were shown to be recognized by human T cells (24 of 31), even though many were not immunogenic in the HLA-A2 transgenic murine models (only 14 of 31 were immunogenic in HLA-A2 transgenic mice). Most importantly, the immune responses induced by vaccines encoding the conserved, HLA-A2 supertype-restricted influenza epitopes were broadly protective against challenges with both the highly murine virulent H1N1 PR8 strain, and a less virulent mouse-adapted H3N2 viral strain. These HLA-A2-restricted CD8+ T cell responses were protective even though the vaccines did not include any known neutralizing antibody epitopes. Therefore, this work also provides further proof-of-concept for the overall strategy focused on the development of T cell targeting universal influenza vaccines. Additional work already is ongoing to identify highly conserved CD8+ T cell epitopes restricted by the five other major HLA class I supertypes.

The development and refinement of immunoinformatic tools has allowed for the identification of numerous T cell epitopes for a variety of pathogens. In fact, several T cell-based multi-epitope vaccines have been generated and proven to be highly successful in mice expressing human MHC (McMurry et al., 2007; Gregory et al., 2009; Moise et al., 2013). Human T cell epitope-based vaccine trials so far have not always been as convincing. For example, an epitope-based vaccine for HIV failed to generate measurable T cell responses in humans (Gorse et al., 2008; Wilson et al., 2003; Wilson et al., 2008). However, in this epitope-based HIV vaccine study, the only CD4+ T cell epitope included in the DNA vaccine (PADRE) failed to induce immune responses in most of the subjects, suggesting a deficiency in the vaccine delivery platform or specific construct itself. Other efforts to induce T cell immunity in humans have been more successful. For example, several epitope-based vaccines for various cancers have proven immunogenic (Lennerz et al., 2014; Asahara et al., 2013; Dangooe et al., 2010; Kenter et al., 2009; Bocchia et al., 2005; Ott et al., 2017; Sahin et al., 2017). Recently, an artificial recombinant protein expressing a very limited number of CD4+ and CD8+ T cell influenza epitopes was shown to induce T cell responses, and enhanced later HA-based immune responses in human subjects (Atsmon et al., 2012; Atsmon et al., 2014).

Currently, approved influenza vaccines are designed to induce robust B cell (antibody) immunity against the major viral surface protein hemagglutinin (HA) and to a lesser extent neuraminidase (NA). However, because antigenic drift (and shift) in the HA and NA antigens result in subtle conformational changes, antibodies do not generally exhibit potent cross-strain neutralization activity. In contrast, internal antigens M1, M2, and NP are highly conserved among diverse influenza A strains, and T cells recognizing these conserved antigens can recognize and protect against infection with diverse influenza strains. Furthermore, parallel studies have found that antibodies directed against conserved regions within the HA stalk can provide cross-strain protective immunity (Krammer et al., 2013; Pica et al., 2012). It is therefore important to consider combining conserved T cell epitope and broadly neutralizing Ab epitopes into future universal influenza vaccine constructs to induce the most broadly heterotypic protective immunity.

Other groups have generated multi-epitope vaccines which have provided partial protection against influenza challenge (e.g., references Ichihashi et al., 2011; Alexander et al., 2010). However, the invention presented here is different in at least four major ways. First, the present approach is focused on identifying epitopes expressed and conserved across highly diverse IAV strains including seasonal and potential pandemic avian and swine strains. In contrast, some but not all of the epitopes reported in previous publications are in fact poorly conserved. Therefore, the vaccine constructs generated using the present approach are likely to have more broadly protective effects than previously described vaccines. Second, previously reported IAV class II epitopes are, in general, native linear IAV sequences. The present class II immunoinformatic strategy relies on the identification of core conserved promiscuous 9-mers which are then extended in both directions to include additional epitopes from multiple strains and subtypes, resulting in longer and denser epitope-rich immunogens with broader influenza coverage. Vaccines incorporating these longer, promiscuous ICS are thus anticipated to have high universal relevance at both the pathogen and human host levels. Third, the present approach goes beyond conventional analysis of influenza 9-mer sequences for HLA binding potential by additionally evaluating the effect of T cell epitopes that are homologous with human protein epitopes on the T cell receptor-facing side of binding 9-mers. These homologies are a natural means of viral camouflage whereby pathogens induce regulatory T cells to suppress protective cellular and antibody responses and evade immune clearance (De Groot et al., 2014). The JanusMatrix algorithm was developed and validated to account for potential homologies with human sequences on the TCR-face of HLA-binding 9-mers. In one application of JanusMatrix, a Treg-inducing epitope was identified in poorly immunogenic H7N9 HA, and improved cellular and humoral responses to a novel HA engineered to delete the epitope (Liu et al., 2015; Wada et al., 2017). In addition, examining cross-conservation with self may reduce the potential for unexpected off-target effects such as were observed for a known cancer epitope (MAGE A3—EVDPIGHLY). A post-hoc JanusMatrix analysis was performed, and a peptide found in human cardiac tissues (titin—ESDPIVAQY), which shares predicted HLA binding and sequence homology with TCR-facing amino acids with the MAGE A3 epitope, was identified. This is of great importance, since two individuals receiving adoptive immunotherapies of MAGE A3-specific T cells died within five days of transfer as a result of titin-autoreactive T cells causing cardiovascular toxicity (Linette et al., 2013; Cameron et al., 2013). Therefore, it is important to examine the TCR-face of T cell epitopes for cross-conservation with the TCR facing residues of similarly HLA-restricted self epitopes when selecting epitopes to include in a universal influenza vaccine. Finally, arrangement of synthetic genes can be complicated, and due to the nature of compiling multiple epitopes with dense HLA binding motifs, new artificial epitopes may be introduced at epitope junctions (neo-epitopes). To address this issue, the VaxCAD algorithm that minimizes junctional immunogenicity and creation of neo-epitopes was used to optimize the construction of synthetic genes.

In conclusion, T cell-targeted vaccines composed of multiple panDR- and HLA-A2 restricted, highly conserved influenza epitopes are immunogenic and protective in mice expressing the appropriate human MHC. Future studies to identify conserved influenza T cell epitopes restricted by additional MHC I supertypes should be prioritized to rapidly generate T cell-based vaccines relevant for all diverse human populations.

II. DEFINITIONS

The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

An "epitope," also known as an antigenic determinant, is the part of a macromolecule that is recognized by the immune system, specifically by antibodies, B cell receptors, or T cell receptors.

"Major histocompatibility complex" or "MHC" is a cluster of genes that plays a role in control of the cellular interactions responsible for physiologic immune responses. In humans, the MHC complex is also known as the HLA complex. For a detailed description of the MHC and HLA complexes (see Paul, 1993).

"Human leukocyte antigen" or "HLA" is a human class I or class II major histocompatibility complex (MHC) protein (see, e.g., Stites, 1994).

An "HLA supertype or family," as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like supertype molecules (where xx denotes a particular HLA type) are synonyms.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "supermotif" is a peptide binding specificity shared by HLA molecules encoded by two or more HLA alleles. Thus, a supermotif preferably is recognized with high or intermediate affinity (as defined herein) by two or more HLA antigens.

"Cross-reactive binding" indicates that a peptide is bound by more than one HLA molecule; a synonym is degenerate binding.

A "protective immune response" refers to a T cell response to an antigen derived from an infectious agent, which prevents or at least partially arrests disease symptoms or infection. The immune response may also include an antibody response that has been facilitated by the stimulation of helper T cells.

III. INFLUENZA VIRUS

A. General

The etiological cause of influenza, the Orthomyxoviridae family of viruses, was first discovered in pigs by Richard Shope in 1931. This discovery was shortly followed by the isolation of the virus from humans by a group headed by Patrick Laidlaw at the Medical Research Council of the United Kingdom in 1933. However, it was not until Wendell Stanley first crystallized tobacco mosaic virus in 1935 that the non-cellular nature of viruses was appreciated.

The first significant step towards preventing influenza was the development in 1944 of a killed-virus vaccine for influenza by Thomas Francis, Jr. This built on work by Australian Frank Macfarlane Burnet, who showed that the virus lost virulence when it was cultured in fertilized hen's eggs. Application of this observation by Francis allowed his group of researchers at the University of Michigan to develop the first influenza vaccine, with support from the U.S. Army. The Army was deeply involved in this research due to its experience of influenza in World War I, when thousands of troops were killed by the virus in a matter of months.

Although there were scares in the State of New Jersey in 1976 (with the Swine Flu), worldwide in 1977 (with the Russian Flu), and in Hong Kong and other Asian countries in 1997 (with H5N1 avian influenza), there have been no major pandemics since the 1968 Hong Kong Flu. Immunity to previous pandemic influenza strains and vaccination may have limited the spread of the virus and may have helped prevent further pandemics.

The influenza virus is an RNA virus of the family Orthomyxoviridae, which comprises five genera: Influenzavirus A, Influenzavirus B, Influenzavirus C, Isavirus and Thogotovirus. The Influenzavirus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are:

H1N1, which caused Spanish flu in 1918 and has been identified as the serotype of the 2009 outbreak of swine flu originating from Mexico H2N2, which caused Asian Flu in 1957

H3N2, which caused Hong Kong Flu in 1968

H5N1, a pandemic threat in the 2007-08 flu season

H7N7, which has unusual zoonotic potential

H1N2, endemic in humans and pigs

H9N2

H7N2

H7N3

H10N7

Influenza viruses bind to cells through sialic acid sugars on the surfaces of epithelial cells; typically in the nose, throat, and lungs of mammals and intestines of birds. The cell imports the virus by endocytosis. In the acidic endosome, part of the viral hemagglutinin protein fuses the viral envelope with the vacuole's membrane, releasing the viral RNA (vRNA) molecules, accessory proteins, and RNA-dependent RNA polymerase into the cytoplasm. These proteins and vRNA form a complex that is transported into the cell nucleus, where the RNA-dependent RNA polymerase begins transcribing complementary positive-sense vRNA. The vRNA is either exported into the cytoplasm and translated, or remains in the nucleus. Newly-synthesized viral proteins are either secreted through the Golgi apparatus onto the cell surface or transported back into the nucleus to bind vRNA and form new viral genome particles. Other viral proteins have multiple actions in the host cell, including degrading cellular mRNA and using the released nucleotides for vRNA synthesis and also inhibiting translation of host-cell mRNAs.

Negative-sense vRNAs that form the genomes of future viruses, RNA-dependent RNA polymerase, and other viral proteins are assembled into a virion. Hemagglutinin and neuraminidase molecules cluster into a bulge in the cell membrane. The vRNA and viral core proteins leave the nucleus and enter this membrane protrusion. The mature virus buds off from the cell in a sphere of host phospholipid membrane, acquiring hemagglutinin and neuraminidase with this membrane coat. As before, the viruses adhere to the cell through hemagglutinin; the mature viruses detach once their neuraminidase has cleaved sialic acid residues from the host cell. After the release of new influenza viruses, the host cell dies.

Because of the absence of RNA proofreading enzymes, the RNA-dependent RNA polymerase makes a single nucleotide insertion error roughly every 10 thousand nucleotides, which is the approximate length of the influenza vRNA. Hence, the majority of newly-manufactured influenza viruses are mutants, causing "antigenic drift." The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

B. The 1918 "Spanish" Flu

The 1918 flu pandemic, commonly referred to as the Spanish Flu, was an influenza pandemic that spread to nearly every part of the world. It was caused by an unusually virulent and deadly Influenza A virus strain of subtype H1N1. Historical and epidemiological data are inadequate to identify the geographic origin of the virus. Most of its victims were healthy young adults, in contrast to most influenza outbreaks which predominantly affect juvenile, elderly, or otherwise weakened patients. The pandemic lasted from March 1918 to June 1920, spreading even to the Arctic and remote Pacific islands. It is estimated that anywhere from 20 to 100 million people were killed worldwide, or the approximate equivalent of one third of the population of Europe, more than double the number killed in World War I. This extraordinary toll resulted from the extremely high illness rate of up to 50% and the extreme severity of the symptoms, suspected to be caused by cytokine storms. The pandemic is estimated to have affected up to one billion people—half the world's population at the time.

Scientists have used tissue samples from frozen victims to reproduce the virus for study. Among the conclusions of this research is that the virus kills via a cytokine storm, an overreaction of the body's immune system, which explains its unusually severe nature and the concentrated age profile of its victims. The strong immune systems of young adults ravaged the body, whereas the weaker immune systems of children and middle-aged adults caused fewer deaths.

The global mortality rate from the 1918/1919 pandemic is not known, but is estimated at 2.5 to 5% of those who were infected died. Note this does not mean that 2.5-5% of the human population died; with 20% or more of the world population suffering from the disease to some extent, a case-fatality ratio this high would mean that about 0.5-1% ($\approx$50 million) of the whole population died. Influenza may have killed as many as 25 million in its first 25 weeks. Older estimates say it killed 40-50 million people while current estimates say 50 million to 100 million people worldwide were killed. This pandemic has been described as "the greatest medical holocaust in history" and may have killed more people than the Black Death.

As many as 17 million died in India, about 5% of India's population at the time. In Japan, 23 million persons were affected, and 390,000 died. In the U.S., about 28% of the population suffered, and 500,000 to 675,000 died. In Britain as many as 250,000 died; in France more than 400,000. In Canada approximately 50,000 died. Entire villages perished in Alaska and southern Africa. Estimates for the fatalities in the capital city, Addis Ababa, range from 5,000 to 10,000, with some experts opining that the number was even higher, while in British Somaliland one official there estimated that 7% of the native population died from influenza. In Australia an estimated 12,000 people died and in the Fiji Islands, 14% of the population died during only two weeks, and in Western Samoa 22%.

This huge death toll was caused by an extremely high infection rate of up to 50% and the extreme severity of the symptoms, suspected to be caused by cytokine storms. Indeed, symptoms in 1918 were so unusual that initially influenza was misdiagnosed as dengue, cholera, or typhoid. One observer wrote, "One of the most striking of the complications was hemorrhage from mucous membranes, especially from the nose, stomach, and intestine. Bleeding from the ears and petechial hemorrhages in the skin also occurred." The majority of deaths were from bacterial pneumonia, a secondary infection caused by influenza, but the virus also killed people directly, causing massive hemorrhages and edema in the lung.

The unusually severe disease killed between 2 and 20% of those infected, as opposed to the more usual flu epidemic mortality rate of 0.1%. Another unusual feature of this pandemic was that it mostly killed young adults, with 99% of pandemic influenza deaths occurring in people under 65, and more than half in young adults 20 to 40 years old. This is unusual since influenza is normally most deadly to the very young (under age 2) and the very old (over age 70) and may have been due to partial protection caused by exposure to a previous Russian flu pandemic of 1889. Another oddity was that this influenza outbreak was widespread in summer and fall (in the Northern Hemisphere). Typically, influenza is worse in the winter months.

People without symptoms could be stricken suddenly and within hours be too weak to walk; many died the next day. Symptoms included a blue tint to the face and coughing up blood caused by severe obstruction of the lungs. In some cases, the virus caused an uncontrollable hemorrhaging that filled the lungs, and patients drowned in their body fluids (pneumonia). In others, the flu caused frequent loss of bowel control and the victim would die from losing critical intestinal lining and blood loss.

In fast-progressing cases, mortality was primarily from pneumonia, by virus-induced consolidation. Slower-progressing cases featured secondary bacterial pneumonias, and there may have been neural involvement that led to mental disorders in a minority of cases. Some deaths resulted from malnourishment and even animal attacks in overwhelmed communities.

One theory is that the virus strain originated at Fort Riley, Kansas, by two genetic mechanisms—genetic drift and antigenic shift—in viruses in poultry and swine which the fort bred for food; the soldiers were then sent from Fort Riley to different places around the world, where they spread the disease. However, evidence from a recent reconstruction of the virus suggests that it jumped directly from birds to humans, without traveling through swine.

An effort to recreate the 1918 flu strain (a subtype of avian strain H1N1) was a collaboration among the Armed Forces Institute of Pathology, Southeast Poultry Research Laboratory and Mount Sinai School of Medicine in New York; the effort resulted in the announcement (on Oct. 5, 2005) that the group had successfully determined the virus's genetic sequence, using historic tissue samples recovered by pathologist Johan Hultin from a female flu victim buried in the Alaskan permafrost and samples preserved from American soldiers.

Kobasa et al. (2007) reported that monkeys (*Macaca fascicularis*) infected with the recreated strain exhibited classic symptoms of the 1918 pandemic and died from a cytokine storm—an overreaction of the immune system. This may explain why the 1918 flu had its surprising effect on younger, healthier people, as a person with a stronger immune system would potentially have a stronger overreaction. In December, 2008 research by Yoshihiro Kawaoka of University of Wisconsin linked the presence of three specific genes (termed PA, PB1, and PB2) and a nucleoprotein derived from 1918 flu samples to the ability of the flu virus to invade the lungs and cause pneumonia. The combination triggered similar symptoms in animal testing.

C. The 2009 "Swine" Flu

The 2009 swine flu outbreak is an epidemic that began in April 2009 with a new strain of influenza virus. The new strain is commonly called swine flu, but some parties object to the name and it has also been referred to as Mexican flu, swine-origin influenza, North American influenza, and 2009 H1N1 flu. On Apr. 30, 2009, the World Health Organization called it influenza A(H1N1). The outbreak is believed to have started in March 2009. Local outbreaks of an influenza-like illness were first detected in three areas of Mexico, but the virus responsible was not clinically identified as a new strain until Apr. 24, 2009. Following the identification, its presence was soon confirmed in various Mexican states and in Mexico City. Within days, isolated cases (and suspected cases) were identified elsewhere in Mexico, the U.S., and several other Northern Hemisphere countries.

By Apr. 28, 2009, the new strain was confirmed to have spread to Spain, the United Kingdom, New Zealand, and Israel, and the virus was suspected in many other nations, with a total of over 3,000 candidate cases, prompting the World Health Organization (WHO) to change its pandemic alert phase to "Phase 5," which denotes "widespread human infection." Despite the scale of the alert, the WHO stated on Apr. 29, 2009 that the majority of people infected with the virus have made a full recovery without need of medical attention or anti-viral drugs. The common human H1N1 influenza virus affects millions of people every year according to the WHO, causing 250,000 and 500,000 deaths every year around the world. In industrialized countries, most of these deaths occur in those 65 or older.

In March and April 2009, over 3000 cases of suspected swine flu in humans were detected in Mexico and the southwestern United States. The disease was detected in several countries on multiple continents within weeks of its initial discovery. The strain appears to be unusually lethal in Mexico but not in other countries. There have also been cases reported in the states of San Luis Potosi, Hidalgo, Queretaro, and Mexico State. The Mexican fatalities are mainly young adults of 25 to 45, a common trait of pandemic flu.

The CDC has confirmed that U.S. cases contained genetic elements from four different flu viruses—North American swine influenza, North American avian influenza, human influenza, and swine influenza virus typically found in Asia and Europe—"an unusually mongrelised mix of genetic sequences." Pigs have been shown to act as a potential "mixing vessel" in which reassortment can occur between flu viruses of several species. This new strain appears to be a result of the reassortment of two swine influenza viruses, which themselves are descended from previous reassortments in pigs. Influenza viruses readily undergo reassortment because their genome is split between eight pieces of RNA (see Orthomyxoviridae). The virus was resistant to amantadine and rimantadine, but susceptible to oseltamivir (Tamiflu®) and zanamivir (Relenza®).

Gene sequences for every viral gene were made available through the Global Initiative on Sharing Avian Influenza Data (GISAID). Preliminary genetic characterization found that the hemagglutinin (HA) gene was similar to that of swine flu viruses present in U.S. pigs since 1999, but the neuraminidase (NA) and matrix protein (M) genes resembled versions present in European swine flu isolates. The six genes from American swine flu are themselves mixtures of swine flu, bird flu, and human flu viruses. While viruses with this genetic makeup had not previously been found to be circulating in humans or pigs, there is no formal national surveillance system to determine what viruses are circulating in pigs in the U.S. The seasonal influenza strain H1N1 vaccine is thought to be unlikely to provide protection.

The CDC has not fully explained why the U.S. cases were primarily mild disease while the Mexican cases had led to multiple deaths. However, research on previous pandemic strains has suggested that mortality can vary widely between different countries, with mortality being concentrated in the developing world. Differences in the viruses or co-infection are also being considered as possible causes. Of the fourteen initial samples from Mexico tested by the CDC, seven matched the American strain. The virus likely passes through several cycles of infection with no known linkages between patients in Texas and California, and that containment of the virus is "not very likely."

D. Diagnosis

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include:

Body aches, especially joints and throat

Extreme coldness and fever

Fatigue

Headache

Irritated watering eyes

Reddened eyes, skin (especially face), mouth, throat and nose

Abdominal pain (in children with influenza B)

It can be difficult to distinguish between the common cold and influenza in the early stages of these infections, but a flu can be identified by a high fever with a sudden onset and extreme fatigue. Diarrhea is not normally a symptom of influenza in adults, although it has been seen in some human cases of the H5N1 "bird flu" and can be a symptom in children.

Since anti-viral drugs are effective in treating influenza if given early, it can be important to identify cases early. Of the symptoms listed above, the combinations of fever with cough, sore throat and/or nasal congestion can improve diagnostic accuracy. Two decision analysis studies suggest that during local outbreaks of influenza, the prevalence will be over 70%, and thus patients with any of these combinations of symptoms may be treated with neuramidase inhibitors without testing. Even in the absence of a local outbreak, treatment may be justified in the elderly during the influenza season as long as the prevalence is over 15%.

The available laboratory tests for influenza continue to improve. The United States Centers for Disease Control and Prevention (CDC) maintains an up-to-date summary of available laboratory tests. According to the CDC, rapid diagnostic tests have a sensitivity of 70-75% and specificity of 90-95% when compared with viral culture. These tests may be especially useful during the influenza season (prevalence=25%) but in the absence of a local outbreak, or peri-influenza season (prevalence=10%).

Influenza's effects are much more severe and last longer than those of the common cold. Most people will recover in about one to two weeks, but others will develop life-threatening complications (such as pneumonia). Influenza, however, can be deadly, especially for the weak, old, or chronically ill. The flu can worsen chronic health problems. People with emphysema, chronic bronchitis, or asthma may experience shortness of breath while they have the flu, and influenza may cause worsening of coronary heart disease or congestive heart failure. Smoking is another risk factor associated with more serious disease and increased mortality from influenza.

Common symptoms of the flu such as fever, headaches, and fatigue come from the huge amounts of proinflammatory cytokines and chemokines (such as interferon or tumor necrosis factor) produced from influenza-infected cells. In contrast to the rhinovirus that causes the common cold, influenza does cause tissue damage, so symptoms are not entirely due to the inflammatory response. This massive immune response can produce a life-threatening cytokine storm. This effect has been proposed to be the cause of the unusual lethality of both the H5N1 avian influenza, and the 1918 pandemic strain (see above).

In some cases, an autoimmune response to an influenza infection may contribute to the development of Guillain-Barré syndrome. However, as many other infections can increase the risk of this disease, influenza may only be an important cause during epidemics. This syndrome can also be a rare side-effect of influenza vaccines, with an incidence of about one case per million vaccinations.

People with the flu are advised to get plenty of rest, drink plenty of liquids, avoid using alcohol and tobacco and, if necessary, take medications such as paracetamol (acetaminophen) to relieve the fever and muscle aches associated with the flu. Children and teenagers with flu symptoms (particularly fever) should avoid taking aspirin during an influenza infection (especially influenza type B), because doing so can lead to Reye's syndrome, a rare but potentially fatal disease of the liver. Since influenza is caused by a virus, antibiotics have no effect on the infection; unless prescribed for secondary infections such as bacterial pneumonia, they may lead to resistant bacteria. Anti-viral medication can be effective, but some strains of influenza can show resistance to the standard anti-viral drugs (see below).

IV. INFLUENZA PEPTIDES

A. Influenza Virus Structural Proteins

As discussed above, the three major genera of influenza virus are Influenzavirus A, B, and C. Influenzavirus A has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses.

Influenzavirus B has one species, influenza B virus. Influenza B almost exclusively infects humans and is less common than influenza A. The only other animals known to be susceptible to influenza B infection are the seal and the ferret. This type of influenza mutates at a rate 2-3 times lower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

Influenzavirus C has one species, influenza C virus, which infects humans, dogs, and pigs, sometimes causing both severe illness and local epidemics. However, influenza C is less common than the other types and usually only causes mild disease in children.

Influenzaviruses A, B, and C are very similar in overall structure. The virus particle is 80-120 nanometres in diameter and usually roughly spherical, although filamentous forms can occur. These filamentous forms are more common in influenza C, which can form cordlike structures up to 500 micrometres long on the surfaces of infected cells. However, despite these varied shapes, the viral particles of all influenza viruses are similar in composition. These are made of a viral envelope containing two main types of glycoproteins, wrapped around a central core. The central core contains the viral RNA genome and other viral proteins that package and protect this RNA.

Unusually for a virus, its genome is not a single piece of nucleic acid; instead, it contains seven or eight pieces of segmented negative-sense RNA, each piece of RNA contains either one or two genes. For example, the influenza A genome contains 11 genes on eight pieces of RNA, encoding for 11 proteins: hemagglutinin (HA), neuraminidase (NA), nucleoprotein (NP), M1, M2, NS1, NS2(NEP), PA, PB1, PB1-F2, and PB2.

Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for anti-viral drugs. Furthermore, they are antigens to which antibodies can be raised. Influenza A viruses are classified into subtypes based on antibody responses to HA and NA. These different types of HA and NA form the basis of the H and N distinctions in, for example, H5N1. There are 16 H and 9 N subtypes known, but only H1, H2, and H3, and N1 and N2 are commonly found in humans.

B. Peptide Compositions

As used herein, an "amino acid" or "amino acid residue" refers to any naturally-occurring amino acid, any amino acid derivative, or any amino acid mimic known in the art, including modified or unusual amino acids. In certain embodiments, the natural residues of the peptide are sequential, without any non-amino acid interrupting the sequence of natural amino acid residues. In other embodiments, the sequence may comprise one or more non-natural amino acid moieties.

The peptides of the present invention can be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), Houghten et al. (1985). In some embodiments, peptide synthesis is contemplated by using automated peptide synthesis machines, such as those available from Applied Biosystems (Foster City, CA). The peptides of the present invention may be isolated and extensively dialyzed to remove undesired small molecular weight molecules and/or lyophilized for more ready formulation into a desired vehicle.

The term "peptide" is used interchangeably with "oligopeptide" in the present specification to designate a series of residues, typically L-amino acids, connected one to the other, typically by peptide bonds between the α-amino and carboxyl groups of adjacent amino acids. Particular T cell-inducing oligopeptides of the invention are 25 residues or less in length and usually consist of between about 8 and about 25 residues, particularly 9 to 15 residues. Specific lengths of 8, 9, 10, 11, 12, 13, 14, 15, 16, 17, 18, 19, 20, 21, 22, 23, 24, and 25 residues are contemplated.

An "immunogenic peptide" or "peptide epitope" is a peptide which comprises an allele-specific motif or supermotif such that the peptide will bind an HLA molecule and induce a T cell response. Thus, immunogenic peptides of the invention are capable of binding to an appropriate HLA molecule and thereafter inducing a T cell response to the antigen from which the immunogenic peptide is derived.

Modified or unusual amino acid include, but are not limited to, those shown in Table A.

TABLE A

| Abbr. | Modified and Unusual Amino Acids |
|---|---|
| | Amino Acid |
| Aad | 2-Aminoadipic acid |
| Baad | 3- Aminoadipic acid |
| Bala | 2-alanine, -Amino-propionic acid |
| Abu | 2-Aminobutyric acid |
| 4Abu | 4- Aminobutyric acid, piperidinic acid |
| Acp | 6-Aminocaproic acid |
| Ahe | 2-Aminoheptanoic acid |
| Aib | 2-Aminoisobutyric acid |

TABLE A-continued

| Abbr. | Modified and Unusual Amino Acids |
|---|---|
| | Amino Acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| Ahyl | Allo-Hydroxylysine |
| 3Hyp | 3-Hydroxyproline |
| 4Hyp | 4-Hydroxyproline |
| Ide | Isodesmosine |
| Aile | Allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In particular embodiments, biocompatible protein, polypeptide, or peptide containing compositions will generally be mammalian proteins or peptides or synthetic proteins or peptides each essentially free from toxins, pathogens, and harmful immunogens.

C. Variants

The present invention also contemplates modification of the peptides shown in Tables 3 and 4. Such peptide "variants" may include additional residues, such as additional N- or C-terminal amino acids, or altered/substituted/modified amino acids, and yet still comprise one of the sequences disclosed herein, so long as the sequence meets the criteria set forth above, including the maintenance of biological activity.

The following is a discussion based upon changing the amino acids of a peptide to create a variant peptide. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine, and isoleucine.

A specialized kind of insertional variant is the fusion protein. This molecule generally has all or a substantial portion of the native molecule, linked at the N- or C-terminus, to all or a portion of a second peptide or polypeptide. In particular, embodiments where multiple peptides of the present invention (SEQ ID NOs: 1-56) are linked in a "head-to-tail" fashion to create a polytope molecule, i.e., an epitope multimer. The peptides may be linked to each directly though peptide bonds, or they may be separated by peptide "spacers," or they may be attached using non-peptide or peptoid "linker," which are well known in the art. In addition, inclusion of a cleavage site at or near the fusion junction or linker will facilitate removal or release of other peptide sequences. Other useful fusions include linking of functional domains, such as active sites from enzymes such as a hydrolase, glycosylation domains, cellular targeting signals, or transmembrane regions.

D. Peptide Purification

In certain embodiments, the peptides of the present invention may be purified. The term "purified peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein/peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an HLA-restricted peptide of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. Although this preparation will be purified in an inactive form, the denatured material will still be capable of transducing cells. Once inside of the target cell or tissue, it is generally accepted that the polypeptide will regain full biological activity.

As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

V. VACCINE PROTOCOLS AND FORMULATIONS

In an embodiment of the present invention, a method of treatment and prevention of influenza by the delivery of a peptide or peptide-encoding composition is contemplated. An effective amount of the vaccine composition, generally, is defined as that amount sufficient to detectably and repeatedly ameliorate, reduce, minimize or limit the extent of the disease or condition or symptoms thereof. More rigorous definitions may apply, including elimination, eradication, or cure of disease.

A. Administration

The peptides of the present invention may be used in vivo to produce anti-influenza virus immune response, and thus constitute therapeutic and prophylactic vaccines. Also, nucleic acids encoding peptides of the present invention may be used in vivo to produce anti-influenza virus immune response. Thus, the peptides or nucleic acids can be formulated for parenteral administration, e.g., formulated for injection via the intradermal, intravenous, intramuscular, subcutaneous, or intraperitoneal routes. Administration by the intradermal and intramuscular routes are specifically contemplated. The vaccine can also be administered by a topical route directly to the mucosa, for example by nasal drops or mist, inhalation, or by nebulizer.

The present invention also provides methods for inducing antigen-presenting cells using the peptides of this invention. The antigen-presenting cells can be induced by inducing dendritic cells from peripheral blood monocytes; and then contacting (stimulating) them with the peptides of this invention, in vitro or in vivo. Administering the peptides of this invention to subjects induces in the body of the subject antigen-presenting cells to which the peptides of this invention are immobilized. Alternatively, the peptides of this invention can be immobilized to the antigen-presenting cells to be administered to the subject as a vaccine.

Some variation in dosage and regimen will necessarily occur depending on the age and medical condition of the subject being treated, as well as the route chosen. The person responsible for administration will, in any event, determine the appropriate dose for the individual subject. In many instances, it will be desirable to have multiple administrations of the vaccine. Thus, the compositions of the invention may be administered 1, 2, 3, 4, 5, 6, 7, 8, 9, 10, or more times. The administrations will normally be at from one to twelve-week intervals, more usually from one to six-week intervals. Periodic re-administration will be desirable with recurrent exposure to the pathogen.

The administration may use various "unit doses." Unit dose is defined as containing a predetermined-quantity of the therapeutic composition. The quantity to be administered, and the particular route and formulation, are within the skill of those in the clinical arts.

B. Measuring Immune Responses

One of ordinary skill would know various assays to determine whether an immune response against a peptide was generated. The phrase "immune response" includes both cellular and humoral immune responses. Various B lymphocyte and T lymphocyte assays are well known, such as ELISAs, cytotoxic T lymphocyte (CTL) assays, such as chromium release assays, proliferation assays using peripheral blood lymphocytes (PBL), tetramer assays, and cytokine production assays. See Benjamini et al. (1991), hereby incorporated by reference.

C. Injectable Formulations

One method for the delivery of a pharmaceutical according to the present invention is via injection. However, the pharmaceutical compositions disclosed herein may alternatively be administered intravenously, intradermally, intramuscularly, or even intraperitoneally as described in U.S. Pat. Nos. 5,543,158; 5,641,515 and 5,399,363 (each specifically incorporated herein by reference in its entirety).

Injection may be by syringe or any other method used for injection of a solution, as long as the agent can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, or sodium chloride. Prolonged absorption of the injectable compositions can be brought about by the use in the compositions of agents delaying absorption, for example, aluminum monostearate and gelatin. Sterile aqueous media that can be employed will be known to those of skill in the art in light of the present disclosure. For example, one dosage may be dissolved in 1 mL of isotonic NaCl solution and either added to 1000 mL of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous injectable composition that contains a protein as an active ingredient is well understood in the art.

D. Inhalable or Aerosol Formulations

A particular mode of administration contemplated by the inventor for the peptides of the present invention is via inhalation and/or administration to the nasal mucosa, i.e., intranasal administration. A variety of commercial vaccines (influenza, measles) are currently administered using a nasal mist formulation. The methods of the present invention can be carried out using a delivery similar to that used with the Flu-Mist® product, which employs the BD AccuSpray® System (Becton Dickinson). Also useful for this route are nebulizers, such as jet nebulizers and ultrasonic nebulizers.

E. Additional Vaccine Components

In other embodiments of the invention, the antigenic composition may comprise an additional immunostimulatory agent. Immunostimulatory agents include but are not limited to an additional antigens, an immunomodulator, an antigen presenting cell or an adjuvant. In other embodiments, one or more of the additional agent(s) is covalently bonded to the antigen or an immunostimulatory agent, in any combination.

1. Adjuvants

As also well known in the art, the immunogenicity of a particular immunogen composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. Suitable molecule adjuvants include all acceptable immunostimulatory compounds, such as cytokines, toxins, or synthetic compositions.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant. Other adjuvants that may also be used include IL-1, IL-2, IL-4, IL-7, IL-12, interferon, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion also is contemplated. MHC antigens may even be used.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° C. to about 101° C. for a 30 second to 2-minute period, respectively. Aggregation by reactivating with pepsin-treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is muramyl dipeptide (N-acetylmuramyl-L alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

BCG (*bacillus* Calmette-Guerin, an attenuated strain of *Mycobacterium*) and BCG-cell wall skeleton (CWS) may also be used as adjuvants, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945. BCG is an important clinical tool because of its immunostimulatory properties. BCG acts to stimulate the reticulo-endothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE BCG (Organon Inc., West Orange, NJ).

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present invention.

Another group of adjuvants are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA), and glycerol teichoic acid (GTA). Active forms of their synthetic counterparts may also be employed in connection with the invention (Takada et al., 1995).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Adjuvants may be encoded by a nucleic acid (e.g., DNA or RNA). It is contemplated that such adjuvants may be also be encoded in a nucleic acid (e.g., an expression vector) encoding the antigen, or in a separate vector or other construct. Nucleic acids encoding the adjuvants can be delivered directly, such as for example with lipids or liposomes.

2. Biological Response Modifiers

In addition to adjuvants, it may be desirable to co-administer biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

3. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-α, MIP1-β, IP-10 and combinations thereof. The skilled artisan will recognize that certain cytokines (e.g., IFN's) are also known to have chemoattractant effects and could also be classified under the term chemokines.

4. Immunogenic Carrier Proteins

The use of peptides for antibody generation or vaccination may require conjugation of the peptide to an immunogenic carrier protein, such as hepatitis B surface antigen, keyhole limpet hemocyanin, or bovine serum albumin. Means for conjugating a polypeptide or peptide to an immunogenic carrier protein are well known in the art and include, for example, glutaraldehyde, m-maleimidobenzoyl-N-hydroxysuccinimide ester, carbodiimide, and bis-biazotized benzidine. Other immunopotentiating compounds are also contemplated for use with the compositions of the invention such as polysaccharides, including chitosan, which is described in U.S. Pat. No. 5,980,912, hereby incorporated by reference. Also, multiple (more than one) peptides may be crosslinked to one another (e.g., polymerized).

F. Combination Treatments

In certain embodiments, it may prove useful to use the vaccines of the present invention in conjunction with an anti-viral therapy. Two well-known classes of anti-virals are neuraminidase inhibitors and M2 inhibitors (adamantane derivatives). Neuraminidase inhibitors are currently preferred for flu virus infections. The CDC recommended against using M2 inhibitors during the 2005-06 influenza season.

Anti-viral drugs such as oseltamivir (Tamiflu®) and zanamivir (Relenza®) are neuraminidase inhibitors that are designed to halt the spread of the virus in the body. These drugs are often effective against both influenza A and B and have been shown to be effective in combatting the recently emerged 2009 "swine" flu. The Cochrane Collaboration reviewed these drugs and concluded that they reduce symptoms and complications. Different strains of influenza viruses have differing degrees of resistance against these anti-virals, and it is impossible to predict what degree of resistance a future pandemic strain might have.

The anti-viral drugs amantadine and rimantadine are designed to block a viral ion channel (M2 protein) and prevent the virus from infecting cells. These drugs are sometimes effective against influenza A if given early in the infection but are always ineffective against influenza B. Measured resistance to amantadine and rimantadine in American isolates of H3N2 has increased to 91% in 2005. In contrast to neuraminidase inhibitors, amantadine and rimantadine have not proven effect again the 2009 "swine" flu.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials & Methods

Mice and Viruses: HLA-DR1 transgenic mice, expressing a chimeric mouse:human class II element (I-Ed/HLA-DR1), crossed onto a MHC-II deficient B6 background, were obtained from E. Rosloniec (University of Tennessee Health Science Center) (Rosloniec et al., 1997). HLA-A2 HHD mice, expressing a chimeric H-2Db/HLA-A2.1 molecule and deficient in murine MHC-I expression, and HLA-A2/DR1 dual transgenic mice, deficient in endogenous murine MHC-I and II, expressing full-length HLA-DR1 and chimeric H-2Db/HLA-A2.1 were obtained under MTA from the Institut Pasteur (Pascolo et al., 1997; Pajot et al., 2004). All strains were bred at Saint Louis University under germ-limiting conditions. Male and female mice, aged 6-12 weeks, were utilized as described in each experiment. Mouse-adapted influenza strains A/Puerto Rico/8/34 (H1N1) and A/Victoria/3/75 (H3N2) were provided by Andrew Pekosz (Johns Hopkins University) and Donald Smee (Utah State University), respectively, and propagated in MDCK cells (ATCC, Manassas, VA) with DMEM supplemented with penicillin, streptomycin, L-glutamine, 0.5% bovine serum albumin, and trypsin TPCK (1 µg/mL). Viral stocks were stored frozen (−80° C.) and were quantified after thawing using 50% tissue culture infectious dose assays ($TCID_{50}$). Briefly, titrations of sample were added to 96-well tissue culture plates previously seeded with MDCK cells to >80% confluence in the media above. After 3 days of culture, cells were fixed, stained with formalin and crystal violet, and cytopathic effect (CPE) observed microscopically.

Immunoinformatics: Strains causing major pandemics (such as the 1918 pandemic strain) and epidemics over the last 40+ years, as well as more novel strains (e.g., H5 and H7 strains) shown to be highly virulent in humans were identified. M1, M2, and NP protein sequences from selected influenza A virus strains were collected from the Influenza Virus Resource and the GISAID EpiFlu Database (see Table 1 for list of 53 influenza strains used for immunoinformatic analyses, and Table 2 for accession numbers and reference laboratories) (Shu & McCauley, 2017; Bao et al., 2008; Brister et al., 2015). The Conservatrix algorithm, which searches for identically matched segments and tracks the number of strains in which regions (9-mers) are conserved, was used to identify conserved 9-mer sequences in M1, M2, and NP sequences from the 53 input strains (DeGroot et al., 2009). Potential immunogenicity of parsed 9-mers was computationally assessed by epitope mapping using the EpiMatrix algorithm.

Promiscuous epitopes were identified for eight common human MHC II alleles (DRB1*0101, DRB1*0301, DRB1*0401, DRB1*0701, DRB1*0801, DRB1*1101, DRB1*1301, and DRB1*1501), which are cumulatively expressed by >95% of the human population. 9-mer sequences scoring above 1.64 on the EpiMatrix "Z" scale, typically the top 5% of scores, are likely MHC ligands and considered potential epitope "hits." The EpiMatrix score for all eight Class II alleles served as the starting point for constructing immunogenic consensus sequences (ICS). ICS were constructed using EpiAssembler, an algorithm that maximizes epitope density in a 20-25 amino acid long sequence by assembling overlapping 9-mers that are both >70% conserved and predicted to be immunogenic. Design of vaccine immunogens with increased epitope density makes it possible for presentation of epitopes to T cells in the context of more than one HLA allele, thereby more broadly covering the HLA diverse human population. Furthermore, it enables increased coverage of influenza strains. Epitopes were ranked based on influenza strain coverage (all >70%) and EpiMatrix scores for DRB*0101. To minimize risks of inducing unanticipated immune responses (Treg cells, autoimmunity), ICS epitopes sharing significant homology with human sequences were triaged using JanusMatrix, an advanced algorithm that identifies MHC binding peptides predicted to present structural patterns to TCR similar to "self" peptides (Moise et al., 2015; Liu et al., 2015; Losikoff et al., 2015; De Groot et al., 2014; Moise et al., 2013).

A similar immunoinformatic approach was employed to identify highly conserved influenza A HLA-A2-restricted 9-mer T cell epitopes capable of inducing robust heterotypic protective immunity. Using the suite of immunoinformatic tools described above (Conservatrix, EpiMatrix), M1, M2, and NP sequences from the 53 diverse influenza A strains (H1/H2/H3/H5/H7/H9) shown in Table 1 were analyzed for both conservation and predicted binding to HLA*0201, representative of the HLA-A2 supertype expressed by ~50% of humans. BlastP analyses were performed to identify (and remove) potential human homologues.

Vaccines: Peptide-pulsed dendritic cell (DC) vaccines were prepared as described previously (Eickhoff et al., 2015). Briefly, $5 \times 10^6$ B16-Flt3L cells were injected i.p. into donor mice, and 2 weeks later DC were matured in vivo by lipopolysaccharide (LPS) injection (2 µg i.v.). Splenic DC isolated 14-16 hours later using Miltenyi CD11c+ microbeads were pulsed for 1-2 hours at 37° C. with various peptide pools (2.5 µg/mL each peptide). DC vaccine recipient mice were immunized using $0.5$-$1.0 \times 10^6$ peptide-pulsed DC delivered i.v. In experiments involving HLA-A2 transgenic mice, DC were additionally pulsed with pan-restricted PADRE and OVA323-339 peptides to induce $CD4^+$ T cell helper responses to optimize $CD8^+$ T cell responses.

Conserved influenza promiscuous ICS or HLA-A2 epitopes were arranged into synthetic minigenes for DNA vaccine preparation using VaxCAD, an algorithm that optimizes the order of epitopes in a vaccine construct to minimize the creation and introduction of non-specific epitopes at influenza epitope junctions (De Groot et al., 2005). The protein sequences were next reverse-engineered for high expression in mice/humans (i.e., codon harmonized) and cloned into commercially available antibiotic-free, sucrose-selectable, eukaryotic-expression plasmids (Nature Technology Corporation). Promiscuous ICS were cloned in frame with the human tissue plasminogen activator (TPA) leader sequence to target the protein for secretion. Predicted HLA-A2 epitopes were cloned with a ubiquitin leader optimized for intracellular protein degradation. An additional construct was engineered to express promiscuous $CD4^+$ T cell epitopes PADRE and OVA323-339 using the TPA construct described above. Endotoxin-free plasmid DNAs were prepared using QIAGEN EndoFree Plasmid Giga kits, and suspended in PBS for immunization studies. Mice were anesthetized by i.p. injection of ketamine (60 mg/kg) and xylazine (5 mg/kg) prior to i.m. delivery of 100 µg of each DNA into the tibialis anterior muscle beds (50 µg/limb).

Murine T cell analyses: Conserved ICS/epitope-specific T cell responses were studied by IFN-γ ELISPOT as described previously (Eickhoff et al., 2015). T cell subsets were prepared using Miltenyi CD4 and CD8 microbeads according to the manufacturer's recommendations and suspended in complete media (RPMI 1640 with 10% heat-inactivated FBS, 2 mM L-glutamine, non-essential amino acids, 1 mM sodium pyruvate, 50 U/mL penicillin, 50 μg/mL streptomycin, 5 mM HEPES, and 55 nM β-mercaptoethanol). For study of murine MHC class II responses, splenic CD4$^+$ T cells were added to IFN-γ ELISPOT plates ($1 \times 10^5$/well) with syngeneic naïve CD4/CD8 T cell-depleted splenocytes ($3 \times 10^5$/well) and individual peptides or peptide pools (10 μg/mL each peptide). In other cases, total splenocytes were studied using $4 \times 10^5$ total cells/well. Conserved influenza-specific HLA-A2-restricted CD8$^+$ T cell responses were studied similarly using $1 \times 10^5$ CD8$^+$ T cells, $3 \times 10^5$ total naïve splenocytes as APC, and 2.5-5.0 μg/mL of each peptide. After assay development, ELISPOT well images were captured, spots enumerated using a C.T.L. Immuno-Spot Reader and software, and results expressed as spot forming cells (SFC) per million cells. A positive response was defined as a value greater than the mean+2 standard deviations of negative control T cell responses to all individual stimulating peptides.

Human T cell immunogenicity assays: Cryopreserved human peripheral blood mononuclear cells (PBMC) were prepared from heparinized blood, and HLA-A2 expression in each volunteer was determined by flow cytometry (anti-HLA-A2 clone BB7.2). Thawed PBMC were stimulated in 96-well "U" bottom plates ($2.5 \times 10^5$ cells/well) with individual peptide (10 μg/mL) in 0.2 mL X-Vivo15 media (Lonza) supplemented with 2 mM L-glutamine and penicillin/streptomycin (50 U/mL and 50 μg/mL, respectively). IL-2 was provided on days 0, 3, 7, and 10. On day 13, cells were washed once to remove residual peptide, and the following day cells were washed again, resuspended in complete X-Vivo15 media, and stimulated in overnight IFN-γ ELISPOT assays (50,000 cells/well) with 10 μg/mL peptide. Human IFN-γ ELISPOT assays were conducted as recommended by the manufacturer (BD Biosciences) and data analyzed using a C.T.L. ImmunoSpot system.

Influenza challenge and assessment of protection: Influenza virus preparations prepared as described above were diluted in DMEM and delivered intranasally (20 μL doses split between nares) to mice under ketamine/xylazine-induced anesthesia. Doses for each challenge experiment are described in the brief descriptions of the drawings. Some groups of mice were weighed daily and/or studied for survival, and others euthanized 3-4 days post-challenge for assessment of pulmonary influenza burden. Briefly, lungs were homogenized in 1 mL of DMEM using a Tissue Tearor hand homogenizer (Biospec) and homogenates stored at −80° C. prior to serial dilution and virus quantitation using TCID$_{50}$ assays as described above. HLA-DR1 transgenic mice were extremely susceptible to the PR8 H1N1 strain, preventing the identification of a low enough challenge dose that allowed survival. Instead lung viral titers were used as the primary protection endpoint in HLA-DR1 transgenic mice challenged with H3N2, which is significantly less virulent than H1N1 in our murine model.

Example 2—Immunoinformatic Identification of Putative Pan-DR and HLA-A2-Restricted Conserved Influenza T Cell Epitopes The ultimate goal for influenza vaccinologists is to develop vaccines that could protect against all future influenza epidemics and pandemics (Erbelding et al., 2018). To that end, the inventors first sought to identify highly conserved sequences within the M1, M2, and NP proteins from diverse influenza strains. Influenza strains were identified that have been associated with major pandemics/epidemics, are used commonly in influenza laboratories, have crossed the species barrier (evidence of human infection with known swine or avian influenza viruses), and those that are listed by the WHO as possible future vaccine strains. Fifty-three influenza A strains were identified, for which complete sequences of the M1, M2, and NP proteins were available for subsequent study. The strains were diverse, with sequences collected from H1N1, H2N2, H3N2, H5N1, H7N2, H7N3, H7N7, and H7N9 subtypes (Table 1).

Next, protein sequences were analyzed for conservation and epitope composition. Sequences parsed into 9-mer frames allowed identification of 727 unique M1 9-mers, 573 unique M2 9-mers, and 2,021 unique NP 9-mers from the 53 influenza strains. Promiscuous immunogenic consensus sequences (ICS) were identified for eight common human MHC II HLA-DR alleles cumulatively expressed by >95% of humans. Epitopes were ranked based on influenza strain coverage (all >70%) and EpiMatrix scores for DRB*0101. Thirty ICS selected for further analyses were highly conserved among the influenza strains (average 91.7% conservation among the diverse influenza strains) and were predicted to contain multiple DR-restricted epitopes (average 7.1 epitopes per ICS). These 30 ICS were next examined further to identify MHC binding peptides predicted to present structural patterns to TCR similar to "self" peptides (Moise et al., 2015; Liu et al., 2015; Losikoff et al., 2015; De Groot et al., 2014; Moise et al., 2013). Five of the top 30 predicted ICS were found to share significant sequence homology with human peptides and were excluded from further study. The resulting 25 high-priority conserved influenza ICS (Table 3) were produced as synthetic peptides for immunogenicity evaluation and arranged into a synthetic minigene for DNA vaccine preparation using the EpiVax VaxCAD algorithm (De Groot et al., 2005). The synthetic minigene produces a polypeptide having a sequence according to SEQ ID NO: 57.

Similarly, parsed 9-mers were scored for predicted binding to MHC class I alleles sharing the most common HLA-A2 supertype. Sequences with EpiMatrix HLA-A2 predicted binding scores of ≥1.64 (representing the top 5% of predicted binders), ≥70% conservation (among the 53 input strains), and without significant human homology were selected for further study (shown in Table 4). Most of the selected influenza HLA-A2-restricted sequences were highly conserved (present in 88.3% of the highly diverse influenza A strains listed in Table 1).

Example 3—Immunogenicity and Protective Efficacy of Class II Influenza ICS

To determine immunogenicity of the selected class II ICS, mice expressing the common human class II allele HLA-DR1, and lacking endogenous murine class II (Rosloniec et al., 1997), were vaccinated in a prime-boost fashion with naked DNA and peptide pool-pulsed mature DC (mature DC prepared as described in (Eickhoff et al., 2015)). One month after the final vaccination, splenic CD4$^+$ T cells were isolated and stimulated with APC pulsed with individual peptides (or DMSO control) in IFN-γ ELISPOT assays. As shown in FIG. 1A, 14 of 25 predicted promiscuous panDR-restricted epitopes were immunogenic in HLA-DR1 Tg mice. Similar results were obtained in both female and male vaccinated mice.

To study the protective efficacy of these DNA vaccines encoding highly conserved promiscuous panDR-restricted ICS given alone, groups of HLA-DR1 Tg mice were vaccinated with control or FluICS DNA vaccines. One month after the final vaccination, mice were challenged with mouse-adapted influenza A/Victoria/3/75 H3N2 intranasally (~30×LD$_{50}$), and 4 days later representative mice were euthanized to analyze conserved FluICS peptide pool-specific T cell responses and lung H3N2 viral burden. Splenocytes from mice vaccinated with DNA encoding conserved influenza ICS were responsive to the pool of conserved influenza T cell epitopes (FIG. 1B). Conserved FluICS DNA vaccines provided significant protection as assessed by lung viral burden measured 4 days post-challenge (FIG. 1C, day 4 TCID$_{50}$ assays; P<0.005 by unpaired t-test). Importantly, 50% of FluICS vaccinated HLA-DR1 transgenic mice survived lethal challenge as compared to 0% of control vaccinated mice (FIG. 1D; P<0.05 by Fisher's exact test).

Human T cells were found to be highly reactive with the FluICS peptide pool. PBMC from four different individuals were stimulated in overnight IFN-γ ELISPOT assays with DMSO (control) or FluICS. The PBMC responded strongly to the FluICS peptides as demonstrated in FIG. 5A (P<0.05 by Mann-Whitney U tests). Next, human CD4$^+$ T cells expanded for 1 week with FluICS peptides were re-stimulated with APC pulsed with DMSO (control), FluICS peptides, live H3N2, and live H1N1. As shown in FIG. 5B, CD4$^+$ T cells expanded with FluICS peptides, but not with DMSO alone, were highly responsive to re-stimulation with not only the FluICS peptide pool, but also H3N2- and H1N1-infected APC (N=5; P≤0.05 by both Mann-Whitney U and paired t-tests). Similar significant results were obtained after expanding PBMC for 1 week with live H3N2 and H1N1, and then re-stimulating with the FluICS peptide pool. Taken together, these results indicate that the conserved FluICS are presented to antigen-specific human CD4$^+$ T cells in the context of influenza infection with diverse IAV strains.

Figure 2:
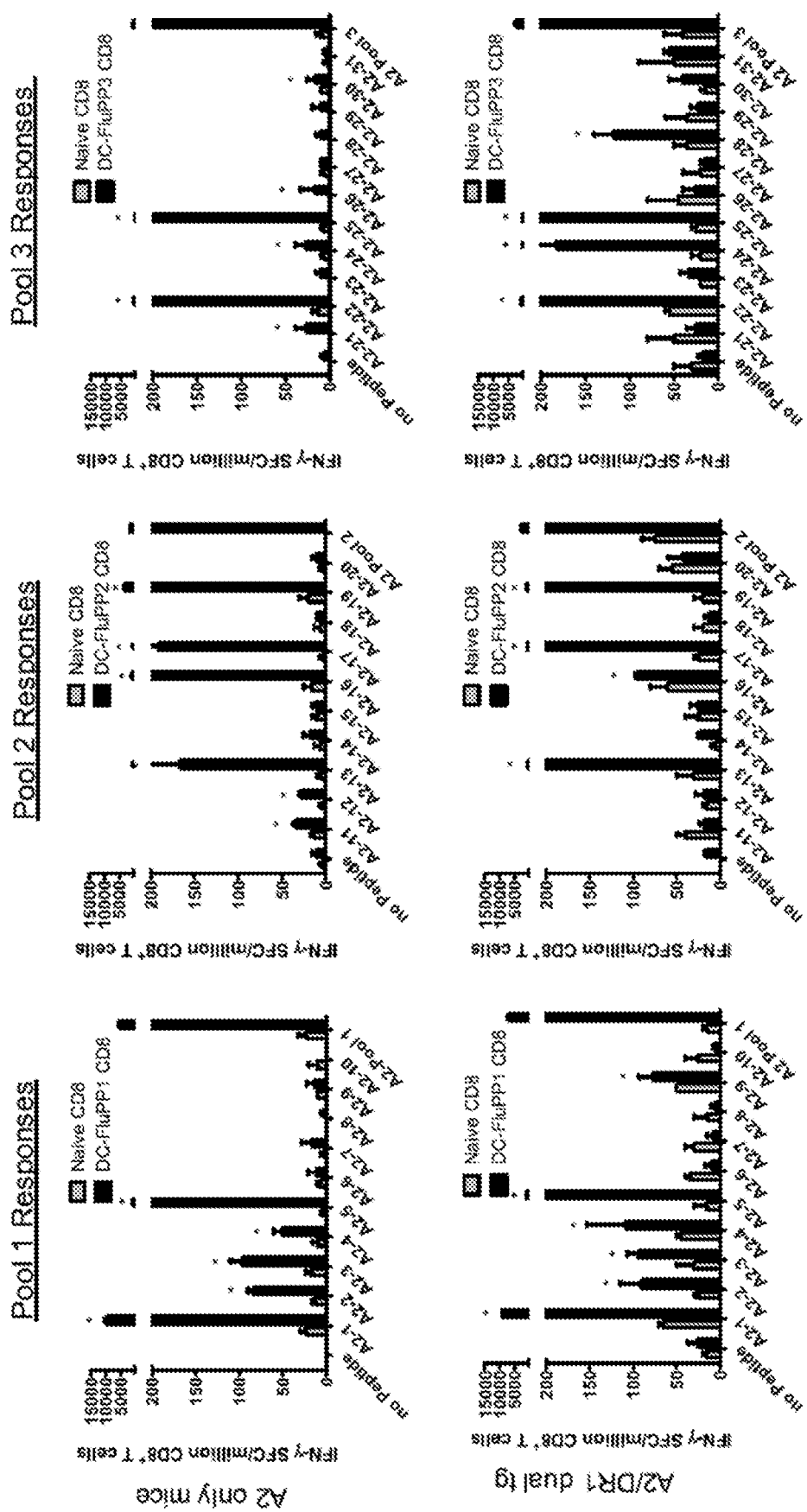
FIG. 2. Immunogenicity of highly conserved HLA-A2-restricted influenza A epitopes in HLA-A2 transgenic mice. Mature dendritic cells (DC) from HLA-A2 and HLA-A2/DR1 transgenic mice were pulsed with pools of 10-11 putative conserved HLA-A2-restricted epitopes and i.v. injected into strain-matched recipient mice. To provide CD4 help for optimal CD8 T cell induction, DCs also were pulsed with the highly promiscuous PADRE and OVA peptides that are immunogenic in all mice. Four weeks after the second vaccination, splenic $CD8^+$ T cells were purified and added to IFN-γ ELISPOT assays along with naïve antigen presenting cells and individual peptides. Shown are results generated with $CD8^+$ T cells purified from 2-3 HLA-A2 (top) and HLA-A2/DR1 transgenic mice (bottom) vaccinated with putative HLA-A2 peptides #1-10 (left panels), #11-20 (middle panels), and #21-31 (right panels). Control stimulations included media alone (no peptide) and the total peptide pool (10-11 peptides) used for vaccination of mice.

Example 4—Immunogenicity and Protective Efficacy of Conserved HLA-A2-Restricted Influenza Epitopes The epitope-MHC binding predictions shown above in Table 4 were validated using a combination of in vivo and in vitro studies. The 31 predicted influenza epitopes were synthesized, pooled (10-11 peptides per pool), pulsed onto matured dendritic cells (professional antigen presenting cells), and injected i.v. into HLA-A2 transgenic mice deficient in endogenous murine MHC I expression (Pascolo et al., 1997; Pajot et al., 2004). To provide CD4 help for optimal CD8$^+$ T cell induction, mice were co-injected with DC pulsed with the highly promiscuous PADRE and OVA peptides that are immunogenic in all mice. Four weeks after the second vaccination, purified splenic CD8$^+$ T cells were stimulated with individual peptides or peptide pools in IFN-γ ELISPOT assays. As shown in FIG. 2, robust T cell responses were induced specific for many of the HLA-A2 predicted epitopes by vaccination with influenza-peptide pulsed dendritic cells in two different strains of mice expressing HLA-A2. Overall, 19 of the 31 predicted HLA-A2-restricted epitopes were immunogenic in these model systems. Similar results were obtained in experiments conducted using both strains of HLA-A2 transgenic mice.

Next, naïve human PBMC immunoreactivity assays were conducted. PBMC collected from HLA-A2 negative and HLA-A2 positive healthy adult donors were expanded in vitro for 14 days with individual influenza peptides. Cells were then washed and restimulated with peptide (or DMSO control) in overnight IFN-γ ELISPOT assays. Shown in FIGS. 3A&B are results obtained from HLA-A2 positive and HLA-A2 negative donors, respectively. Most of the conserved influenza predicted HLA-A2 epitopes did not induce potent responses in HLA-A2 negative PBMC cultures. Minimal responses detected in HLA-A2 negative PBMC could be a result of certain epitopes being immunoreactive across more than one supertype. However, 24 of the 31 conserved influenza peptides predicted to be HLA-A2-restricted T cell epitopes induced a positive response in at least one of the four HLA-A2 positive PBMC sample, confirming the relevance of these epitopes for human influenza immunity.

A DNA vaccine construct encoding each of these 31 predicted HLA-A2 epitopes was designed using VaxCAD (DeGroot et al., 2005), which reduces the creation of new epitopes at epitope junctions. The DNA vaccine produces a polypeptide having a sequence according to SEQ ID NO: 58. Shown in FIG. 4A are predicted epitope and junctional scores for default ordered (top) and optimally ordered (bottom) minigenes. Next, HLA-A2 transgenic mice were vaccinated in a prime/boost fashion with DNA and DC/peptide vaccines. The vaccines were highly immunogenic, inducing robust epitope-specific CD8$^+$ T cell responses in HLA-A2 transgenic mice (FIG. 4B). To study vaccine-induced protective immunity, groups of control and Flu-A2 vaccinated mice were intranasally challenged with 8×LD$_{50}$ of Influenza A/Puerto Rico/8/34 (H1N1), and post-challenge weights and survival monitored. As shown in FIG. 4C, mice immunized with vaccines incorporating highly conserved influenza HLA-A2-restricted epitopes were significantly protected as compared to vaccinated control mice with respect to severe weight loss (P<0.05 by Mann-Whitney U test) and death (P<0.005 by Fisher's exact and Mantel-Cox log rank tests). In order to assess heterotypic protective immunity induced by the Flu-A2 vaccine, groups of vaccinated mice were challenged with A/Victoria/3/75 (H3N2), and lung viral titers determined 3 days post-challenge using TCID$_{50}$ assays. As shown in FIG. 4D, mice receiving vaccines incorporating conserved HLA-A2-restricted influenza A epitopes also were significantly protected against H3N2 challenge as demonstrated by significantly lower post-challenge viral titers (P<0.05 by Mann-Whitney U test). Cumulatively, the results presented in FIGS. 4A-D demonstrate that vaccines incorporating highly conserved influenza epitopes identified using a comprehensive immunoinformatic approach elicit potent T cell responses protective against diverse influenza strain challenges in mice expressing only a single human class I molecule.

TABLE 1

Strains utilized for identification of putative HLA-restricted T cell epitopes.

| Influenza Strain Name | Subtype |
|---|---|
| A/Brevig Mission/1/1918 | H1N1 |
| A/Puerto Rico/8/34 | H1N1 |
| A/WSN/1933 | H1N1 |
| A/New Jersey/76 | H1N1 |
| A/USSR/90/1977 | H1N1 |
| A/Brazil/11/1978 | H1N1 |

TABLE 1-continued

Strains utilized for identification of putative HLA-restricted T cell epitopes.

| Influenza Strain Name | Subtype |
|---|---|
| A/Chile/1/1983 | H1N1 |
| A/Singapore/6/1986 | H1N1 |
| A/Beijing/262/1995 | H1N1 |
| A/New Caledonia/20/1999 | H1N1 |
| A/Brisbane/59/2007 | H1N1 |
| A/California/7/2009 | H1N1 |
| A/Singapore/1/57 | H2N2 |
| A/Japan/170/62 | H2N2 |
| A/Taiwan/64 | H2N2 |
| A/Hong Kong/1/68 | H3N2 |
| A/Udorn/72 | H3N2 |
| A/England/42/72 | H3N2 |
| A/Port Chalmers/1/1973 | H3N2 |
| A/Victoria/3/1975 | H3N2 |
| A/Texas/1/1977 | H3N2 |
| A/Bangkok/1/1979 | H3N2 |
| A/Philippines/2/1982 | H3N2 |
| A/Leningrad/360/1986 | H3N2 |
| A/Sichuan/2/1987 | H3N2 |
| A/Shanghai/11/1987 | H3N2 |
| A/Beijing/353/1989 | H3N2 |
| A/Shangdong/9/1993 | H3N2 |
| A/Johnannesburg/33/1994 | H3N2 |
| A/Nanchang/933/1995 | H3N2 |
| A/Wuhan/359/1995 | H3N2 |
| A/Sydney/5/1997 | H3N2 |
| A/Moscow/10/1999 | H3N2 |
| A/Fujian/411/2002 | H3N2 |
| A/California/7/2004 | H3N2 |
| A/Wisconsin/67/2005 | H3N2 |
| A/Brisbane/10/2007 | H3N2 |
| A/Perth/16/2009 | H3N2 |
| A/Victoria/361/2011 | H3N2 |
| A/Texas/50/2012 | H3N2 |
| A/goose/Guangdong/1/96 | H5N1 |
| A/Hong Kong/156/97 | H5N1 |
| A/Vietnam/1203/2004 | H5N1 |
| A/Indonesia/5/2005 | H5N1 |
| A/turkey/turkey/1/2005 | H5N1 |
| A/Cambodia/R0404050/2007 | H5N1 |
| A/Guizhou/1/2013 | H5N1 |
| A/New York/107/2003 | H7N2 |
| A/mallard/Netherlands/12/2000 | H7N3 |
| A/Canada/504/04 | H7N3 |
| A/Mexico/InDRE7218/2012 | H7N3 |
| A/Hangzhou/1/2013 | H7N9 |
| A/Hong Kong/1073/1999 | H9N2 |

TABLE 2

Accession numbers and reference laboratories.

| Major strains (pandemic/epidemic) | M1 | M2 | NP | GISAID Originating Lab | GISAID Submitting Lab |
|---|---|---|---|---|---|
| A/Brevig Mission/1/1918 | AAN06597 | AAN06598 | AAV48837 | | |
| A/Puerto Rico/8/34 | AFM71847 | AFM71848 | AFM71850 | | |
| A/WSN/1933 | ACF54599 | ACF54600 | ACF54602 | | |
| A/New Jersey/76 | ABQ44395 | ABQ44396 | ABQ44398 | | |
| A/USSR/90/1977 | AFM73478 | AFM73479 | AFM73481 | | |
| A/Brazil/11/1978 | ABO38066 | ABO38067 | ABO38069 | | |
| A/Chile/1/1983 | AFM72055 | AFM72056 | AFM72058 | | |
| A/Singapore/6/1986 | GISAID EPI_ISL_6905 | GISAID EPI_ISL_6905 | GISAID EPI_ISL_6905 | unlisted | unlisted |
| A/Beijing/262/1995 | GISAID EPI_ISL_22625 | GISAID EPI_ISL_22625 | GISAID EPI_ISL_22625 | unlisted | unlisted |
| A/New Caledonia/20/1999 | ABF21304 | ABF21305 | ABF21286 | | |
| A/Brisbane/59/2007 | GISAID EPI_ISL_71838 | GISAID EPI_ISL_71838 | GISAID EPI_ISL_71838 | unlisted | unlisted |
| A/California/7/2009 | GISAID EPI_ISL_31553 | GISAID EPI_ISL_31553 | GISAID EPI_ISL_31553 | Naval Health Research Center | Centers for Disease Control and Prevention |
| A/Singapore/1/57 | ACF54478 | ACF54479 | ACF54481 | | |
| A/Japan/170/62 | AAO46364 | AAO46365 | AAO46435 | | |
| A/Taiwan/64 | ABF21310 | ABF21311 | ABF21289 | | |
| A/Hong Kong/1/68 | AAK51722 | AAK51730 | AAK51731 | | |
| A/Udorn/72 | ABD79033 | ABD79034 | ABD79036 | | |
| A/England/42/72 | AAO46711 | AAO46712 | AAO46552 | | |
| A/Port Chalmers/1/1973 | AFM71946 | AFM71947 | AFM71949 | | |
| A/Victoria/3/1975 | AFM71968 | AFM71969 | AFM71971 | | |
| A/Texas/1/1977 | AFG99106 | AFG99107 | AFG99109 | | |
| A/Bangkok/1/1979 | AFH00715 | AFH00716 | AFH00718 | | |
| A/Philippines/2/1982 | AFG99161 | AFG99162 | AFG99164 | | |
| A/Leningrad/360/1986 | AFM72077 | AFM72078 | AFM72080 | | |
| A/Sichuan/2/1987 | AFM72099 | AFM72100 | AFM72102 | | |
| A/Shanghai/11/1987 | AFM72121 | AFM72122 | AFM72124 | | |
| A/Beijing/353/1989 | AFH00759 | AFH00760 | AFH00762 | | |
| A/Shangdong/9/1993 | AFH00286 | AFH00287 | AFH00289 | | |
| A/Johnannesburg/33/1994 | AFG72549 | AFG72550 | AFG72552 | | |
| A/Nanchang/933/1995 | AFG72626 | AFG72627 | AFG72629 | | |
| A/Wuhan/359/1995 | AFG72670 | AFG72671 | AFG72673 | | |
| A/Sydney/5/1997 | AFG72758 | AFG72759 | AFG72761 | | |
| A/Moscow/10/1999 | AFM72209 | AFM72210 | AFM72212 | | |
| A/Fujian/411/2002 | AFG72824 | AFG72825 | AFG72827 | | |

TABLE 2-continued

Accession numbers and reference laboratories.

| Major strains (pandemic/epidemic) | M1 | M2 | NP | GISAID Originating Lab | GISAID Submitting Lab |
|---|---|---|---|---|---|
| A/California/7/2004 | AFH00638 | AFH00639 | AFH00641 | | |
| A/Wisconsin/67/2005 | AFH00649 | AFH00650 | AFH00652 | | |
| A/Brisbane/10/2007 | ACO95271 | ACO95272 | ACO95274 | | |
| A/Perth/16/2009 | GISAID EPI_ISL_31055 | GISAID EPI_ISL_31055 | GISAID EPI_ISL_31055 | Pathwest QE II Medical Centre | WHO Collaborating Centre for Reference and Research on Influenza |
| A/Victoria/361/2011 | GISAID EPI_ISL_104004 | GISAID EPI_ISL_104004 | GISAID EPI_ISL_104004 | WHO Collaborating Centre for Reference and Research on Influenza | Centers for Disease Control and Prevention |
| A/Texas/50/2012 | GISAID EPI_ISL_129744 | GISAID EPI_ISL_129744 | GISAID EPI_ISL_129744 | Texas Department of State Health Services-Laboratory Services | Centers for Disease Control and Prevention |
| A/goose/Guangdong/1/96 | AAD51928 | AAD51929 | AAD51925 | | |
| A/Hong Kong/156/97 | AAC34265 | AAC34266 | AAC34267 | | |
| A/Vietnam/1203/2004 | AAT70529 | AAT70528 | AAT70630 | | |
| A/Indonesia/5/2005 | GISAID EPI_ISL_5729 | GISAID EPI_ISL_5729 | GISAID EPI_ISL_5729 | unlisted | unlisted |
| A/turkey/turkey/1/2005 | GISAID EPI_ISL_10107 | GISAID EPI_ISL_10107 | GISAID EPI_ISL_10107 | unlisted | unlisted |
| A/Cambodia/R0404050/2007 | ADM95402 | ADM95403 | ADM95349 | | |
| A/Guizhou/1/2013 | GISAID EPI_ISL_135216 | GISAID EPI_ISL_135216 | GISAID EPI_ISL_135216 | WHO Chinese National Influenza Center | WHO Chinese National Influenza Center |
| A/New York/107/2003 | ACC55275 | ACC55276 | ACC55273 | | |
| A/mallard/Netherlands/12/2000 | ABB21742 | ABB21743 | ABB21745 | | |
| A/Canada/504/04 | ABI85001 | ABI85002 | ABI85004 | | |
| A/Mexico/InDRE7218/2012 (MX/7218) | AFQ55692 | AFQ55693 | AFQ55690 | | |
| A/Hangzhou/1/2013 | AGI60298 | AGI60299 | GISAID EPI441000 | Hangzhou Center for Disease Control and Prevention | Hangzhou Center for Disease Control and Prevention |
| A/Hong Kong/1073/1999 | CAC04081 | CAC04080 | CAB95837 | | |

TABLE 3

Conserved influenza A class II-predicted immunogenic consensus sequences.

| Peptide # | Protein and Starting AA | Consensus Sequence (SEQ ID NO) | EpiMatrix Hits | EpiBars? | Conservation (#) |
|---|---|---|---|---|---|
| Flu.ICS-2 | M1-58 | GMLGFVFTLTVPSERGLQ (SEQ ID NO: 1) | 14 | Yes (2) | 1 |
| Flu.ICS-4 | M1-176 | ENRMVLASTTAKAMEQV (SEQ ID NO: 2) | 7 | Yes (1) | 1 |
| Flu.ICS-6 | M1-76 | RRRFVQNALNGNGDPN (SEQ ID NO: 3) | 7 | Yes (1) | 1 |
| Flu.ICS-7 | M1-129 | GLIYNRMGAVTTEAA (SEQ ID NO: 4) | 6 | Yes (1) | 0.72 |
| Flu.ICS-8 | M1-234 | LENLQAYQKRMGVQMQRF (SEQ ID NO: 5) | 6 | Yes (1) | 0.98 |
| Flu.ICS-9 | M1-17 | SGPLKAEIAQRLEDV (SEQ ID NO: 6) | 4 | Yes (1) | 0.91 |

TABLE 3-continued

Conserved influenza A class II-predicted immunogenic consensus sequences.

| Peptide # | Protein and Starting AA | Consensus Sequence (SEQ ID NO) | EpiMatrix Hits | EpiBars? | Conservation (#) |
|---|---|---|---|---|---|
| Flu.ICS-10 | M1-170 | NPLIRHENRMVLAST (SEQ ID NO: 7) | 3 | No | 0.92 |
| Flu.ICS-11 | M1-135 | MGAVTTEVAFGLVCA (SEQ ID NO: 8) | 1 | No | 0.77 |
| Flu.ICS-12 | M1-125 | ASCMGLIYNRMGAVT (SEQ ID NO: 9) | 3 | No | 0.98 |
| Flu.ICS-14 | NP-409 | QPAFSVQRNLPFERVTI (SEQ ID NO: 10) | 11 | Yes (1) | 1 |
| Flu.ICS-15 | NP-113 | KDEIRRIWRQANNGEDAT (SEQ ID NO: 11) | 9 | No | 1 |
| Flu.ICS-16 | NP-51 | DNEGRLIQNSLTIERMVL (SEQ ID NO: 12) | 9 | No | 0.72 |
| Flu.ICS-17 | NP-133 | LTHMMIWHSNLNDTTYQR (SEQ ID NO: 13) | 8 | Yes (1) | 1 |
| Flu.ICS-18 | NP-216 | RTAYERMCNILKGKF (SEQ ID NO: 14) | 6 | Yes (1) | 1 |
| Flu.ICS-19 | NP-261 | RSALILRGSVAHKSCLP (SEQ ID NO: 15) | 8 | Yes (1) | 1 |
| Flu.ICS-20 | NP-145 | DATYQRTRALVRSGM (SEQ ID NO: 16) | 6 | Yes (1) | 1 |
| Flu.ICS-21 | NP-36 | IGRFYIQMCTELKLNDY (SEQ ID NO: 17) | 7 | Yes (1) | 0.98 |
| Flu.ICS-22 | NP-188 | TMVMELIRMIKRGINDRN (SEQ ID NO: 18) | 13 | Yes (2) | 0.75 |
| Flu.ICS-23 | NP-381 | LRSMYWAIRTRSGGNTN (SEQ ID NO: 19) | 7 | Yes (1) | 1 |
| Flu.ICS-24 | NP-301 | IDPFRLLQNSQVYSLIRP (SEQ ID NO: 20) | 14 | Yes (2) | 0.75 |
| Flu.ICS-25 | NP-310 | SQVYSLIRPNENPAHKSQ (SEQ ID NO: 21) | 9 | Yes (1) | 0.96 |
| Flu.ICS-26 | NP-204 | RNFWRGENGRKTRSA (SEQ ID NO: 22) | 4 | Yes (1) | 0.72 |
| Flu.ICS-28 | NP-75 | RNKYLEEHPSAGKDP (SEQ ID NO: 23) | 2 | No | 0.98 |
| Flu.ICS-29 | NP-161 | PRMCSLMQGSTLPRR (SEQ ID NO: 24) | 1 | No | 1 |
| Flu.ICS-30 | NP-220 | ERMCNILKGKFQTAA (SEQ ID NO: 25) | 1 | No | 1 |

TABLE 4

Conserved putative influenza A HLA-A2-restricted epitopes.

| A2 Peptide | Protein and starting AA | Sequence (SEQ ID NO) | Conservation | A0201 Z-score |
|---|---|---|---|---|
| A2-1 | M1-58 | GILGFVFTL (SEQ ID NO: 26) | 0.98 | 3.09 |
| A2-2 | M1-3 | LLTEVETYV (SEQ ID NO: 27) | 0.98 | 2.71 |
| A2-3 | M1-123 | ALASCMGLI (SEQ ID NO: 28) | 0.98 | 2.42 |
| A2-4 | M1-51 | ILSPLTKGI (SEQ ID NO: 29) | 0.98 | 2.36 |
| A2-5 | M1-59 | ILGFVFTLT (SEQ ID NO: 30) | 0.98 | 2.29 |
| A2-6 | M1-130 | LIYNRMGAV (SEQ ID NO: 31) | 0.72 | 2.27 |
| A2-7 | M1-180 | VLASTTAKA (SEQ ID NO: 32) | 1 | 1.96 |
| A2-8 | M1-55 | LTKGILGFV (SEQ ID NO: 33) | 0.98 | 1.95 |
| A2-9 | M1-178 | RMVLASTTA (SEQ ID NO: 34) | 1 | 1.86 |
| A2-10 | M1-116 | ALSYSAGAL (SEQ ID NO: 35) | 0.7 | 1.74 |
| A2-11 | M1-146 | LVCATCEQI (SEQ ID NO: 36) | 0.87 | 1.7 |
| A2-12 | M1-60 | LGFVFTLTV (SEQ ID NO: 37) | 1 | 1.69 |
| A2-13 | M1-138 | VTTEVAFGL (SEQ ID NO: 38) | 0.77 | 1.68 |
| A2-14 | M1-47 | KTRPILSPL (SEQ ID NO: 39) | 1 | 1.67 |
| A2-15 | M1-129 | GLIYNRMGA (SEQ ID NO: 40) | 0.72 | 1.64 |
| A2-16 | M2-35 | ILHLILWIL (SEQ ID NO: 41) | 0.89 | 2.83 |
| A2-17 | M2-34 | GILHLILWI (SEQ ID NO: 42) | 0.91 | 2.66 |
| A2-18 | M2-38 | LILWILDRL (SEQ ID NO: 43) | 0.89 | 2.41 |
| A2-19 | M2-3 | LLTEVETPI (SEQ ID NO: 44) | 0.74 | 2.2 |
| A2-20 | M2-42 | ILDRLFFKC (SEQ ID NO: 45) | 0.92 | 2.08 |
| A2-21 | M2-41 | WILDRLFFK (SEQ ID NO: 46) | 0.92 | 1.91 |
| A2-22 | M2-32 | IIGILHLIL (SEQ ID NO: 47) | 0.91 | 1.74 |
| A2-23 | M2-45 | RLFFKCIYR (SEQ ID NO: 48) | 0.81 | 1.7 |
| A2-24 | NP-55 | RLIQNSLTI (SEQ ID NO: 49) | 0.7 | 2.51 |
| A2-25 | NP-48 | KLSDYEGRL (SEQ ID NO: 50) | 0.74 | 2.46 |
| A2-26 | NP-158 | GMDPRMCSL (SEQ ID NO: 51) | 1 | 2.38 |
| A2-27 | NP-258 | FLARSALIL (SEQ ID NO: 52) | 0.79 | 2.34 |
| A2-28 | NP-357 | KLSTRGVQI (SEQ ID NO: 53) | 0.74 | 2.15 |
| A2-29 | NP-225 | ILKGKFQTA (SEQ ID NO: 54) | 1 | 1.9 |
| A2-30 | NP-328 | LVWMACHSA (SEQ ID NO: 55) | 0.74 | 1.74 |
| A2-31 | NP-263 | ALILRGSVA (SEQ ID NO: 56) | 1 | 1.71 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

Alexander et al., Universal influenza DNA vaccine encoding conserved CD4+ T cell epitopes protects against lethal viral challenge in HLA-DR transgenic mice, Vaccine, 28:664-672, 2010.

Asahara et al., Phase I/II clinical trial using HLA-A24-restricted peptide vaccine derived from KIF20A for patients with advanced pancreatic cancer, J. Transl. Med., 11:291, 2013.

Assarsson et al., "Immunomic analysis of the repertoire of T-cell specificities for influenza A virus in humans," J. Virol., 82:12241-12251, 2008.

Atsmon et al., Safety and immunogenicity of multimeric-001—a novel universal influenza vaccine, J. Clin. Immunol., 32:595, 2012.

Atsmon et al., Priming by a novel universal influenza vaccine (Multimeric-001)—a gateway for improving immune response in the elderly population, Vaccine, 32:5816, 2014.

Bao et al., The influenza virus resource at the National Center for Biotechnology Information, J. Virol., 82:596, 2008.

Belongia et al., Effectiveness of inactivated influenza vaccines varied substantially with antigenic match from the 2004-2005 season to the 2006-2007 season, J. Infect. Dis., 199:159, 2009.

Belshe, The origins of pandemic influenza—lessons from the 1918 virus, N. Engl. J. Med., 353:2209, 2005.

Belshe et al., Live attenuated versus inactivated influenza vaccine in infants and young children, N. Engl. J. Med., 356(7):685-696, 2007.

Belshe & Gruber, Prevention of otitis media in children with live attenuated influenza vaccine given intranasally, Pediatr. Infect. Dis. J., 19(5 Suppl):566-71, 2000.

Benton et al., Heterosubtypic immunity to influenza A virus in mice lacking IgA, all Ig, NKT cells, or γδ T cells, J. Immunol., 166:7437, 2001.

Bocchia et al., Effect of a p210 multipeptide vaccine associated with imatinib or interferon in patients with chronic myeloid leukaemia and persistent residual disease: a multicentre observational trial, Lancet, 365:657, 2005.

Brister et al., NCBI viral genomes resource, Nucleic Acids Res., 43:D571, 2015.

Burke & Trock, Use of influenza risk assessment tool for prepandemic preparedness, Emerg. Infect. Dis., 24(3): 471-477, 2018.

Cameron et al., "Identification of a Titin-derived HLA-A1-presented peptide as a cross-reactive target for engineered MAGE A3-directed T cells," Sci. Transl. Med., 5:197ra03, 2013.

CDC, Seasonal Influenza Vaccine Effectiveness, 2005-2016, 2016 [cited Apr. 25, 2016]. Available on the world wide web at cdc.gov/flu/professionals/vaccination/effectiveness-studies.htm Dangoor et al., Clinical and immunological responses in metastatic melanoma patients vaccinated with a high-dose poly-epitope vaccine, Cancer Immunology, Immunotherapy: CII, 59:863, 2010.

De Groot et al., Immuno-informatics: Mining genomes for vaccine components, Immunol. Cell Biol., 80:255, 2002.

De Groot et al., HIV vaccine development by computer assisted design: the GAIA vaccine, Vaccine, 23:2136, 2005.

De Groot et al., Immunoinformatic comparison of T-cell epitopes contained in novel swine-origin influenza A (H1N1) virus with epitopes in 2008-2009 conventional influenza vaccine, Vaccine, 27:5740, 2009.

De Groot et al., Immunogenic Consensus Sequence T helper Epitopes for a Pan-*Burkholderia* Biodefense Vaccine, Immunome Res., 7:e2, 2011.
De Groot et al., Immune camouflage: relevance to vaccines and human immunology. Human Vaccines & Immunotherapeutics, 10:3570, 2014.
Eickhoff et al., An immunoinformatic approach for identification of *Trypanosoma cruzi* HLA-A2-restricted CD8+ T cell epitopes, Human Vaccines & Immunotherapeutics, 11:2322, 2015.
Eickhoff et al., Highly conserved influenza T cell epitopes induce broadly protective immunity, Vaccine, 37:5371-5381, 2019.
Epstein et al., DNA vaccine expressing conserved influenza virus proteins protective against H5N1 challenge infection in mice, Emerg. Infect. Dis., 8(8):796-801, 2002.
Epstein, Prior H1N1 influenza infection and susceptibility of Cleveland Family Study participants during the H2N2 pandemic of 1957: an experiment of nature, J. Infect. Dis., 193:49, 2006.
Erbelding et al., A Universal Influenza Vaccine: The Strategic Plan for the National Institute of Allergy and Infectious Diseases, J. Infect. Dis., 218:347, 2018.
Fang et al., Mapping spread and risk of avian influenza A (H7N9) in China, Scientific Reports, 3:2722, 2013.
Gregory et al., Epitope-based vaccination against pneumonic tularemia, Vaccine, 27:5299, 2009.
Gorse et al., Safety and immunogenicity of cytotoxic T-lymphocyte poly-epitope, DNA plasmid (EP HIV-1090) vaccine in healthy, human immunodeficiency virus type 1 (HIV-1)-uninfected adults, Vaccine, 26:215, 2008.
Hoft et al., Live and inactivated influenza vaccines induce similar humoral responses, but only live vaccines induce diverse T-cell responses in young children, J. Infect. Dis., 204(6):845-853, 2011.
Ichihashi et al., Cross-protective peptide vaccine against influenza A viruses developed in HLA-A*2402 human immunity model, PLoS ONE, 2011:6. e24626, 2011.
Jameson et al., Human $CD8^+$ and $CD4^+$ T lymphocyte memory to influenza A viruses of swine and avian species, J. Immunol., 162(12):7578-7583, 1999.
Kenter et al., Vaccination against HPV-16 oncoproteins for vulvar intraepithelial neoplasia, N. Engl. J. Med., 361: 1838, 2009.
Koita et al., Confirmation of immunogenic consensus sequence HIV-1 T-cell epitopes in Bamako, Mali and Providence, Rhode Island, Human Vaccines, 2:119, 2006.
Krammer et al., Chimeric hemagglutinin influenza virus vaccine constructs elicit broadly protective stalk-specific antibodies, J. Virol., 87:6542, 2013.
Lennerz et al., Immunologic response to the survivin-derived multi-epitope vaccine EMD640744 in patients with advanced solid tumors. Cancer Immunology, Immunotherapy: CII, 63:381, 2014.
Liang et al., Heterosubtypic immunity to influenza type-a virus in mice—Effector Mechanisms and Their Longevity, J. Immunol., 152:1653, 1994.
Linette et al., Cardiovascular toxicity and titin cross-reactivity of affinity-enhanced T cells in myeloma and melanoma, Blood, 122:863-871, 2013.
Liu et al., H7N9 T-cell epitopes that mimic human sequences are less immunogenic and may induce Treg-mediated tolerance, Human Vaccines & Immunotherapeutics, 11:2241, 2015.
Losikoff et al., HCV epitope, homologous to multiple human protein sequences, induces a regulatory T cell response in infected patients, Journal of Hepatology, 62:48, 2015.
Mbawuike et al., Influenza A subtype cross-protection after immunization of outbred mice with a purified chimeric NS1/HA2 influenza virus protein, Vaccine, 12(14):1340-1348, 1994.
McMichael et al., Cytotoxic T-cell immunity to influenza, N. Engl. J. Med., 309:13, 1983.
McMurry et al., Diversity of *Francisella tularensis* Schu4 antigens recognized by T lymphocytes after natural infections in humans: identification of candidate epitopes for inclusion in a rationally designed tularemia vaccine, Vaccine, 25:3179, 2007.
Moise et al., In silico-accelerated identification of conserved and immunogenic variola/vaccinia T-cell epitopes, Vaccine, 27:6471, 2009.

Moise et al., VennVax, a DNA-prime, peptide-boost multi-T-cell epitope poxvirus vaccine, induces protective immunity against vaccinia infection by T cell response alone, Vaccine, 29:501, 2011.

Moise et al., The two-faced T cell epitope: examining the host-microbe interface with JanusMatrix, Human Vaccines & Immunotherapeutics, 9:1577, 2013.

Moise et al., Universal H1N1 influenza vaccine development: identification of consensus class II hemagglutinin and neuraminidase epitopes derived from strains circulating between 1980 and 2011, Human Vaccines & Immunotherapeutics, 9:1598, 2013.

Moise et al., Immunization with cross-conserved H1N1 influenza CD4+ T-cell epitopes lowers viral burden in HLA DR3 transgenic mice, Human Vaccines & Immunotherapeutics, 9:2060, 2013.

Moise et al., iVAX: An integrated toolkit for the selection and optimization of antigens and the design of epitope-driven vaccines, Human Vaccines & Immunotherapeutics, 11:2312, 2015.

Moutaftsi et al., A consensus epitope prediction approach identifies the breadth of murine $T_{CD8+}$-cell responses to vaccinia virus, Nat. Biotechnol., 24:817, 2006.

Ott et al., An immunogenic personal neoantigen vaccine for patients with melanoma, Nature, 547:217, 2017.

Pajot et al., A mouse model of human adaptive immune functions: HLA-A2.1-/HLA-DR1-transgenic H-2 class I-/class II-knockout mice, Eur. J. Immunol., 34:3060, 2004.

Pascolo et al., HLA-A2.1-restricted education and cytolytic activity of CD8+ T lymphocytes from β2 microglobulin (β2m) HLA-A2.1 monochain transgenic H-2Db β2m double knockout mice, J. Exp. Med., 185:2043, 1997.

Pica et al., Hemagglutinin stalk antibodies elicited by the 2009 pandemic influenza virus as a mechanism for the extinction of seasonal H1N1 viruses, Proc. Natl. Acad. Sci. U.S.A., 109:2573, 2012.

Rosloniec et al., An HLA-DR1 transgene confers susceptibility to collagen-induced arthritis elicited with human type II collagen, J. Exp. Med., 185:1113, 1997.

Sahin et al., Personalized RNA mutanome vaccines mobilize poly-specific therapeutic immunity against cancer, Nature, 547:222, 2017.

Savic et al., "Epitope specific T-cell responses against influenza A in a healthy population," Immunology, 147:165-177, 2016.

Schulman & Kilbourne, Induction of partial specific heterotypic immunity in mice by a single infection with influenza A virus, J. Bacteriol., 89:170, 1965.

Shrestha et al., Estimating the burden of 2009 pandemic influenza A (H1N1) in the United States (April 2009-April 2010), Clin. Infect. Dis., 52(Suppl 1): S75, 2011.

Shu & McCauley, GISAID: Global initiative on sharing all influenza data—from vision to reality, Euro Surveill., 22(13), 2017.

Sonoguchi et al., Cross-subtype protection in humans during sequential, overlapping, and/or concurrent epidemics caused by H3N2 and H1N1 influenza viruses, J. Infect. Dis., 151:81, 1985.

Taubenberger & Morens, 1918 Influenza: the mother of all pandemics, Emerg. Infect. Dis., 12:15, 2006.

Treanor et al., Effectiveness of seasonal influenza vaccines in the United States during a season with circulation of all three vaccine strains, Clin. Infect. Dis., 55:951, 2012.

Ulmer et al., Protective CD4+ and CD8+ T cells against influenza virus induced by vaccination with nucleoprotein DNA, J. Virol., 72(7):5648-5653, 1998.

WHO, Fact sheet No 211—Influenza (Seasonal). 2014. Available on the world wide web at who.int/mediacentre/factsheets/fs211/en/

Wilson et al., Development of a DNA vaccine designed to induce cytotoxic T lymphocyte responses to multiple conserved epitopes in HIV-1, J. Immunol., 171:5611, 2003.

Wilson et al., Clinical phase 1 testing of the safety and immunogenicity of an epitope-based DNA vaccine in human immunodeficiency virus type 1-infected subjects receiving highly active antiretroviral therapy, Clin. Vaccine. Immunol., 15:986, 2008.

What is claimed is:

1. A peptide comprising the sequence of SEQ ID NO: 57 or 58.

2. The peptide of claim 1, wherein said peptide is lyophilized.

3. A nucleic acid encoding the peptide of claim 1.

4. A method of inducing an immune response in a subject, the method comprising administering to the subject the nucleic acid of claim 3.

* * * * *